United States Patent
Shroff et al.

(10) Patent No.: US 10,281,702 B2
(45) Date of Patent: *May 7, 2019

(54) MULTI-FOCAL STRUCTURED ILLUMINATION MICROSCOPY SYSTEMS AND METHODS

(71) Applicant: The United States of America, as represented by Secretary, Depart. of Health and Human Services, Washington, DC (US)

(72) Inventors: Hari Shroff, Washington, DC (US); Andrew York, Bethesda, MD (US)

(73) Assignee: The United States of America as represented by the Secretary of the Department of Health and Human Services, Washington, DC (US)

(*) Notice: Subject to any disclaimer, the term of this patent is extended or adjusted under 35 U.S.C. 154(b) by 0 days.

This patent is subject to a terminal disclaimer.

(21) Appl. No.: 16/053,533

(22) Filed: Aug. 2, 2018

(65) Prior Publication Data
US 2018/0341096 A1 Nov. 29, 2018

Related U.S. Application Data

(60) Continuation of application No. 15/610,906, filed on Jun. 1, 2017, now Pat. No. 10,042,149, which is a division of application No. 14/380,392, filed as application No. PCT/US2013/027413 on Feb. 22, 2013, now Pat. No. 9,696,534.

(60) Provisional application No. 61/602,139, filed on Feb. 23, 2012.

(51) Int. Cl.
G02B 21/00 (2006.01)
G01N 21/64 (2006.01)

(52) U.S. Cl.
CPC ..... *G02B 21/0072* (2013.01); *G01N 21/6458* (2013.01); *G02B 21/004* (2013.01); *G02B 21/0032* (2013.01); *G02B 21/0036* (2013.01); *G02B 21/0076* (2013.01); *G01N 2021/6478* (2013.01); *G01N 2201/0633* (2013.01)

(58) Field of Classification Search
CPC ............ G02B 21/0072; G02B 21/0032; G02B 21/0036; G02B 21/004; G02B 21/0076; G01N 21/6458
See application file for complete search history.

(56) References Cited

U.S. PATENT DOCUMENTS 7,391,565 B2 * 6/2008 Lauer .................. G02B 5/005
250/458.1

* cited by examiner

*Primary Examiner* — Michael C Bryant
(74) *Attorney, Agent, or Firm* — Polsinelli PC

(57) ABSTRACT

A multi-focal structured illumination microscopy (SIM) system for generating multi-focal patterns of a sample is disclosed. The multi-focal SIM system performs a focusing, scaling and summing operation on each multi-focal pattern in a sequence of multi-focal patterns that completely scan the sample to produce a high resolution composite image.

20 Claims, 18 Drawing Sheets

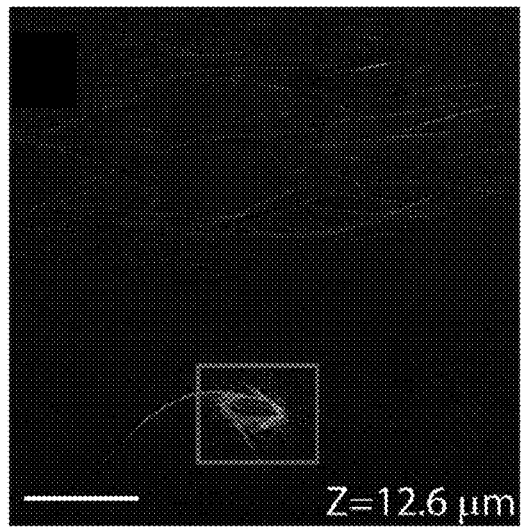
FIG. 17B
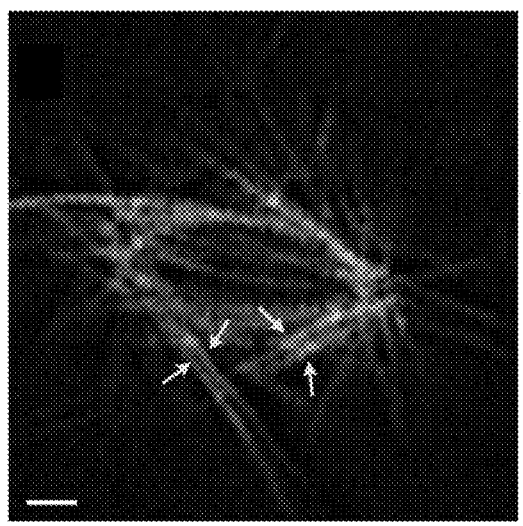
FIG. 17C
FIG. 17D
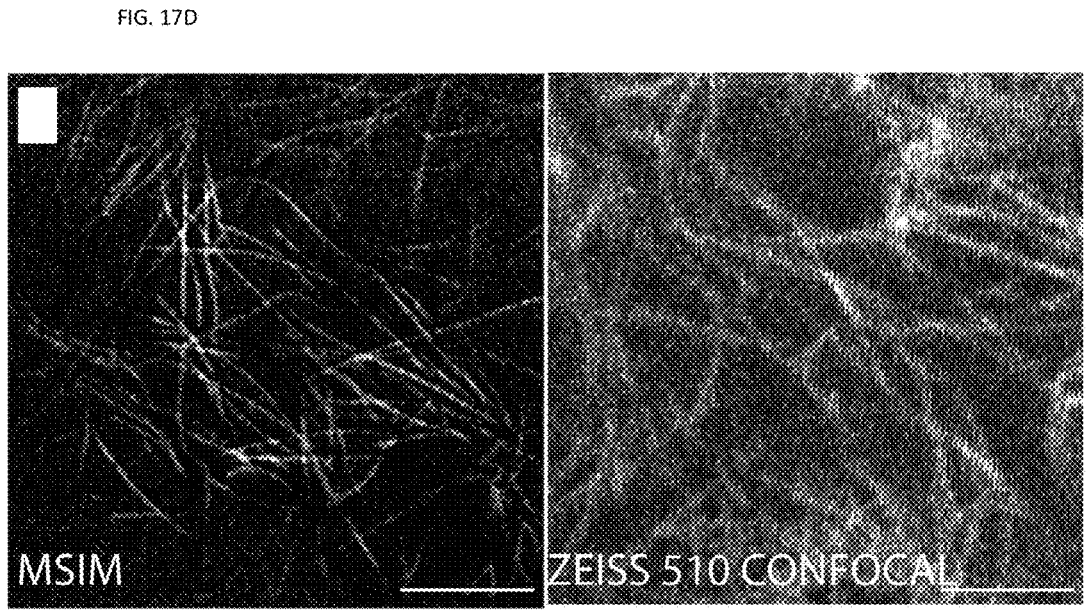

MULTI-FOCAL STRUCTURED ILLUMINATION MICROSCOPY SYSTEMS AND METHODS

CROSS REFERENCE TO RELATED APPLICATIONS

This is a continuation application that claims benefit to U.S. divisional application Ser. No. 15/610,906 filed on Jun. 1, 2017, which claims priority from U.S. non-provisional application Ser. No. 14/380,392 filed on Aug. 22, 2014, which is a 371 of PCT patent application that claims priority from U.S. Provisional Patent Application Ser. No. 61/602,139, filed on Feb. 23, 2012, which are herein incorporated by reference in their entirety.

FIELD

This document relates to multi-focal structured illumination microscopy, and in particular, to multi-focal structured illumination microscopy systems and methods for producing a plurality of multi-focal fluorescent emissions resulting from multi-focal patterns of a sample.

BACKGROUND

Classical fluorescence microscopy is limited in resolution by the wavelength of light, referred to as the "diffraction limit", which restricts lateral resolution to about 200 nm and axial resolution to about 500 nm at typical excitation and emission wavelengths when a sample emits fluorescence that is detected by the microscope. Confocal microscopy is an optical imaging technique used to increase optical resolution beyond the diffraction limit by using point illumination and a spatial pinhole arrangement to eliminate out-of-focus emission light from specimens that are thicker than that of the focal plane, thereby delivering images with 1.41 times the resolution than the diffraction limit by a method that requires tightly closing the pinhole. Unfortunately, closing the pinhole diminishes the signal level of the emitted light from the sample to such an extent as to make this particular method of super-resolution impractical. In addition, a confocal microscope must perfectly align the excitation from the microscope's illumination beam with the pinhole/detector, since a misaligned pinhole results in a reduced and weak light signal being detected as well as resulting in reduced axial optical sectioning of the sample itself. As such, misalignment of the confocal microscope can cause a reduction in the light signal.

A method for resolution enhancement for confocal microscopy has been found that uses an array of detectors, such as pixels in a camera image, wherein each of the detectors in the array produces a separate confocal image. If the array of detectors is sufficiently small, each of the formed confocal images can be equivalent to similar confocal images formed by a confocal microscope with a tightly closed pinhole such that 1.41 times the resolution of the diffraction-limited microscope is achieved when the confocal images are properly aligned. In addition, deconvolution provides a further increase in image resolution. However, this detector array arrangement is limited since only a single excitation point is scanned throughout a two-dimensional plane of the sample, which limits the speed the sample can be scanned and subsequent detection of the fluorescence emissions of the sample.

Another type of microscopy, referred to as structured illumination microscopy (SIM), illuminates a sample with spatially modulated excitation intensity, which is translated and rotated in different positions relative to the sample, with a wide-field image being taken at each translation and rotation. Processing the raw images appropriately results in a final image having double the lateral resolution of conventional wide-field microscopy. Although such SIM systems generate images with 2× the spatial resolution of a conventional microscope, there is still a sacrifice in temporal resolution when producing the final image, as time is required to acquire each of the multiple raw images. SIM may also be used to reject out-of-focus blur, known as "optical sectioning". However, such optical-sectioning is performed computationally, and is thus subject to shot (Poisson) noise. SIM is thus inappropriate for thick or highly stained samples, when background fluorescence may cause this shot noise contribution to overwhelm the in-focus signal.

As such, there is a need in the art for a structured illumination microscopy system that produces a multi-focal excitation pattern of the sample for each high resolution image without sacrificing scanning speed, and that is resistant to the shot noise that may corrupt SIM images.

SUMMARY

In an embodiment, a microscopy system may include a light source for transmitting a single light beam and a beam splitter for splitting the single light beam into a plurality of light beams forming a multi-focal pattern. A scanner scans the plurality of light beams that forms the multi-focal pattern onto a sample such that the sample generates a plurality of fluorescent emissions resulting from each multi-focal pattern. A focusing component then defines an aperture configured to physically block out-of-focus fluorescence emissions of the plurality of fluorescent emissions resulting from each multi-focal pattern and allows through in-focus fluorescent emissions to a pass through the aperture. In addition, a scaling component scales down the plurality of in-focus fluorescent emissions resulting from each multi-focal pattern such that each of the plurality of in-focus fluorescent emissions is scaled down by a predetermined factor to produce a plurality of scaled in-focus fluorescent emissions resulting from each multi-focal pattern. A summing component sums each of the plurality of scaled in-focus fluorescent emissions to produce a plurality of summed, scaled in-focus fluorescent emissions that form a composite image of the plurality of summed, scaled in-focus fluorescent emissions.

In another embodiment, a microscopy system may include a light source for transmitting a single light beam; a beam splitter for splitting the single light beam into a plurality of light beams forming a plurality of multi-focal patterns, wherein each of the plurality of multi-focal patterns defines a plurality of focal points; a scanner for scanning the plurality of light beams that forms each of the plurality of multi-focal patterns onto a sample such that the sample generates a plurality of fluorescent emissions resulting from each of the multi-focal patterns, wherein each of the plurality multi-focal patterns defines a plurality of fluorescent focal points; a detector for collecting the plurality of fluorescent emissions resulting from each of the multi-focal patterns; and a processing system for processing the collected multi-focal fluorescent emissions from the detector comprising: a processor in operative communication with a database for storing the plurality of collected multi-focal fluorescent emissions, wherein the processor removes out-of-focus fluorescent emissions resulting from each of the plurality of multi-focal patterns to leave only in-focus fluorescent emissions resulting from each of the plurality of multi-focal patterns, wherein the processor then scales the in-focus fluorescent emissions resulting from each of the plurality of multi-focal patterns in a local contraction operation in which each of the plurality of fluorescent emissions resulting from each of the multi-focal patterns maintains the same proportional distance from another plurality of fluorescent emissions resulting from the multi-focal pattern as the plurality of fluorescent emissions contract to produce scaled, in-focus fluorescent emissions; wherein the processor sums the plurality of multi-focal in-focus fluorescent emissions to produce a composite image.

In yet another embodiment, a method for multi-focal structured illumination microscopy may include:

generating a single light beam;

splitting the single light beam into a plurality of light beams in which the focal point of each the plurality of light beam forms a plurality of multi-focal patterns, illuminating a sample with the plurality of light beams forming each of the plurality of multi-focal patterns, wherein the illuminated sample produces a plurality of fluorescent emissions resulting from each the plurality of multi-focal patterns;

performing a pinholing operation in which out-of-focus fluorescent emissions from the plurality of fluorescent emissions are blocked and only in-focus fluorescent emissions from the plurality of fluorescent emissions are permitted to pass through during the pinholing operation;

scaling each focal point of the plurality of in-focus fluorescent emissions resulting from the plurality of multi-focal patterns by a predetermined factor to produce a plurality of scaled, in-focus fluorescent emissions resulting from the plurality of multi-focal patterns; and summing each of the plurality of scaled, in-focus fluorescent emissions to form a composite image.

Additional objectives, advantages and novel features will be set forth in the description which follows or will become apparent to those skilled in the art upon examination of the drawings and detailed description which follows.

BRIEF DESCRIPTION OF THE DRAWINGS

FIGS. 17A-17D illustrate various images of a sample using the multi-focal illumination system after pinhole focusing, scaling, and three-dimensional deconvolution.

Corresponding reference characters indicate corresponding elements among the view of the drawings. The headings used in the figures should not be interpreted to limit the scope of the claims.

DETAILED DESCRIPTION

In modern microscopy, structured illumination microscopy (SIM) may be used to examine single cells using spatially patterned light to excite sample fluorescence that is later detected and one or more images processed to produce a super-resolution image with 2× the resolution of a conventional wide-field microscopy image. However, the SIM system sacrifices speed for higher resolution (taking multiple raw images for each super-resolution image). Furthermore, optical-sectioning in a SIM system is performed computationally, and is thus prone to shot noise inherent in fluorescent background. This limits the thickness of the sample that can be examined, thereby requiring other microscopy techniques be used when examining thicker samples. For example, a confocal microscopy system physically rejects out-of-focus light using a pinhole arrangement that allows light from only a particular focal point from the emission light being emitted by the sample to be detected by the system, thereby producing high contrast, optically-sectioned images of relatively thicker samples than can be achieved by a SIM system. The confocal microscope is also capable of providing enhanced resolution relative to conventional wide-field microscopy. However, this enhanced image resolution by the confocal microscope is attained by stopping down the pinhole arrangement, which results in a corresponding prohibitive loss in the fluorescence emission signal being detected from the sample. A modified confocal microscope has been shown to improve image resolution to the resolution level of a SIM system without sacrificing emission signal strength; however, the slow scanning speed attained by the microscope makes it impractical for research purposes.

As such, embodiments of the multi-focal SIM system as set forth herein includes particular components, properties and characteristics that address issues related to achieving high image resolution without sacrificing scanning speed and signal strength required by conventional microscopy imaging systems, and that provides better performance in thick samples than SIM systems that are currently commercially available. The multi-focal SIM system described herein includes particular components that generate a multi-focal excitation pattern for each image taken of the sample to produce a high resolution image at high scanning rates without significant signal loss relative to conventional confocal microscopy and SIM systems. Further details of the multi-focal SIM systems and methods are discussed in greater detail below.

Figure 1:
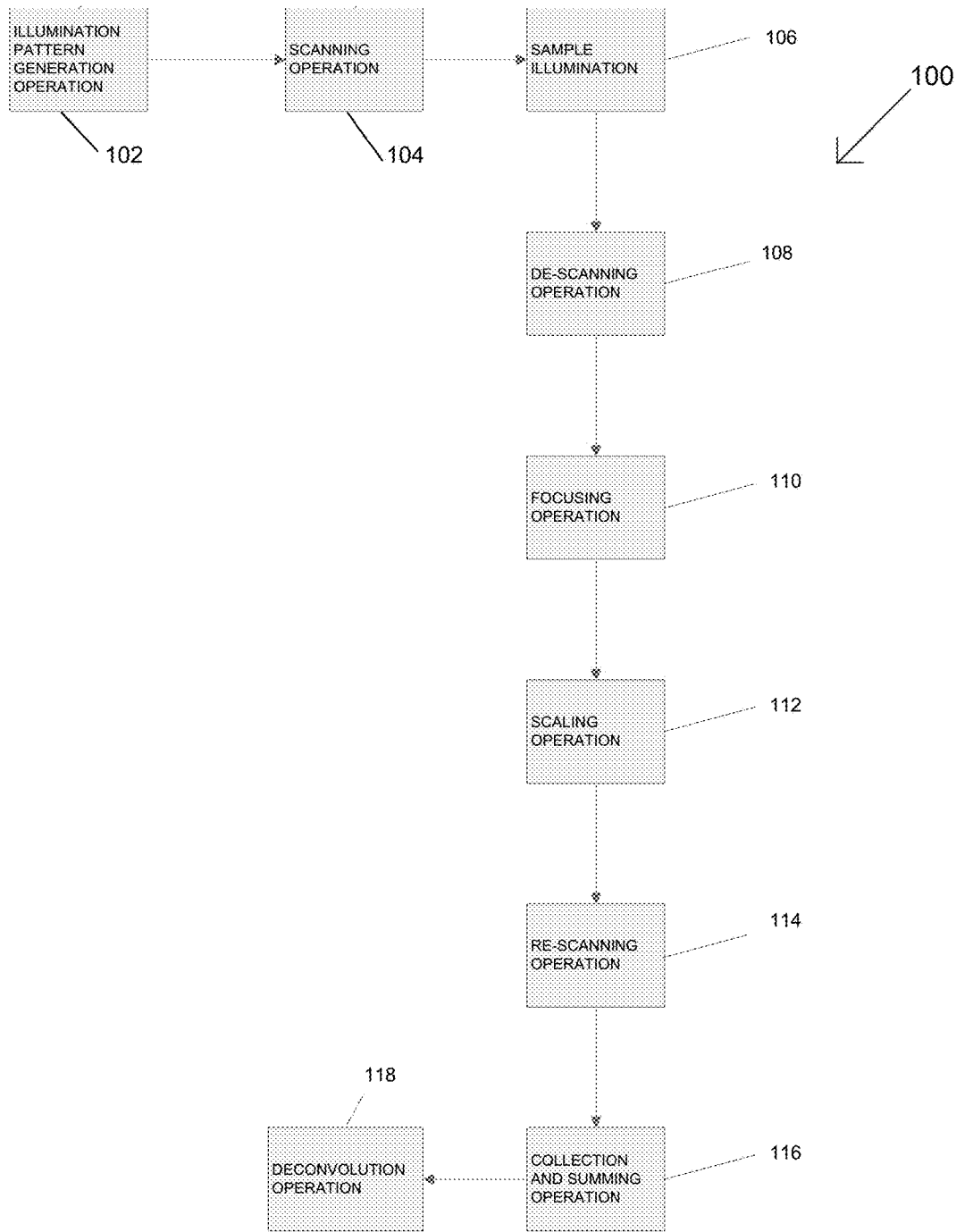
FIG. 1 is a simplified block diagram illustrating one method for generating a multi-focal pattern in a multi-focal structured illumination microscopy (SIM) system.

Referring to the drawings, various embodiments of the multi-focal SIM system are illustrated and generally indicated as 100 and 200 in FIGS. 1-4. As illustrated in FIG. 1, one general embodiment of the multi-focal SIM system, designated 100, is shown. Multi-focal SIM system 100 performs an illumination pattern generation operation 102, which splits a single light beam into a plurality of light beams for generating one or more multi-focal patterns, in which each multi-focal pattern defines an arrangement of focal points for each of the plurality of light beams. For example, a simplified illustration of one example of a multi-focal pattern 170 is shown in FIG. 5. In one embodiment, the multi-focal pattern 170 may include a plurality of focal points 172 arranged in a particular multi-focal pattern 170 defined by the plurality of light beams with each multi-focal pattern 170 defining a different arrangement of focal points for the plurality of light beams such that multi-focal pattern 170 maximizes the distance between any two nearest focal points 172 for a given density of focal points 172, thereby minimizing crosstalk. As used herein, the term crosstalk refers to the ability of nearby light beams to cause excitation and fluorescence from other focal points to appear as if focal points originate from the focal point in question. In a scanning operation 104, the plurality of light beams in each multi-focal illumination pattern are rastered onto a sample 106 being illuminated such that the sample 106 emits a plurality of fluorescent emissions. The fluorescent emissions emitted by the sample 106 are rastered in a de-scanning operation 108 which redirects the plurality of fluorescent emissions for removal of out-of-focus fluorescent emissions in a focusing operation 110. In the focusing operation 110, out-of-focus fluorescent emissions are blocked and only in-focus fluorescent emissions are allowed to pass through for processing.

Figure 6:
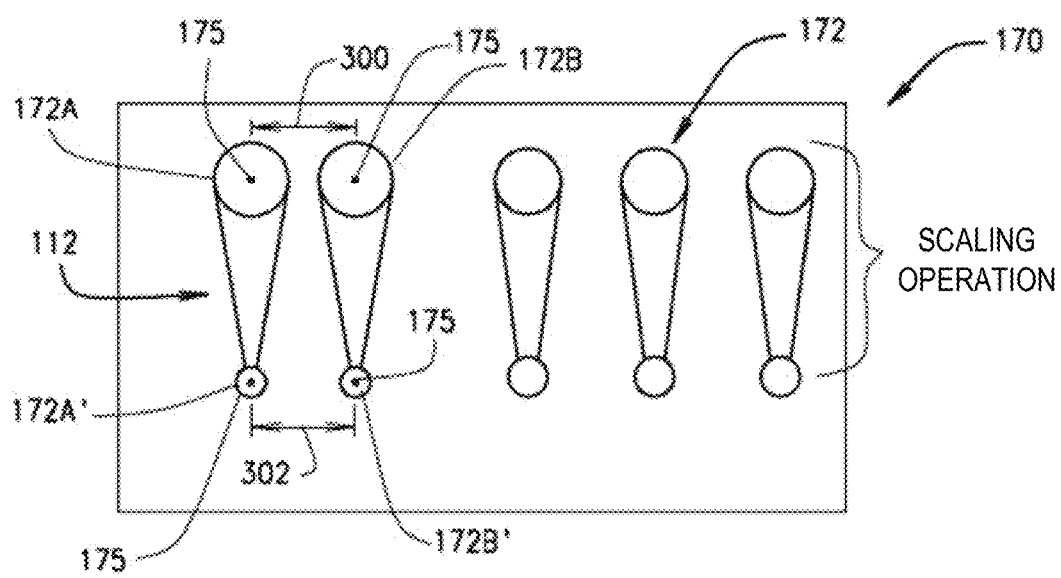
FIG. 6 is a simplified illustration showing a scaling operation that scales in-focus fluorescent emissions resulting from a multi-focal pattern emitted by a sample.

The in-focus fluorescent emissions caused by each multi-focal pattern are then scaled using a scaling operation 112 that locally contracts each of fluorescent emissions by a predetermined factor. In one embodiment of the scaling operation 112 illustrated in FIG. 6, a local contraction of the fluorescent foci 172 caused in a single multi-focal pattern 170 occurs. For example, the local contraction of fluorescent foci 172A and 172B to scaled fluorescent foci 172A' and 172B', respectively, in the multi-focal pattern 170 is such that the distance 300 between the geometric centers 175 of fluorescent foci 172A and 172B and the distance 302 of fluorescent foci 172A and 172B remains the same regardless of the degree of scaling applied to the fluorescent foci 172 of the multi-focal pattern 170. In other words, the scaling operation 112 contracts the fluorescent foci 172 locally without inversion while keeping the relative distances between each of the fluorescent foci the same. After the scaling operation 112, the scaled in-focus fluorescent emissions for each multi-focal illumination pattern are then rastered in a rescanning operation 114 that allows the contracted, in-focus fluorescent emissions caused by each multi-focal pattern to be collected by a detector and summed to produce a composite high resolution image in a collection and summing operation 116.

In some embodiments, after the collection and summing operation 116 the composite image may undergo a deconvolution operation 118 that performs a level of de-blurring that further enhances the resolution of the composite image. The deconvolution operation 118 may be any conventional deconvolution operation 118, such as the freely available Piotyr Wendykier's Parallel Iterative Deconvolution Plugin.

Figure 2:
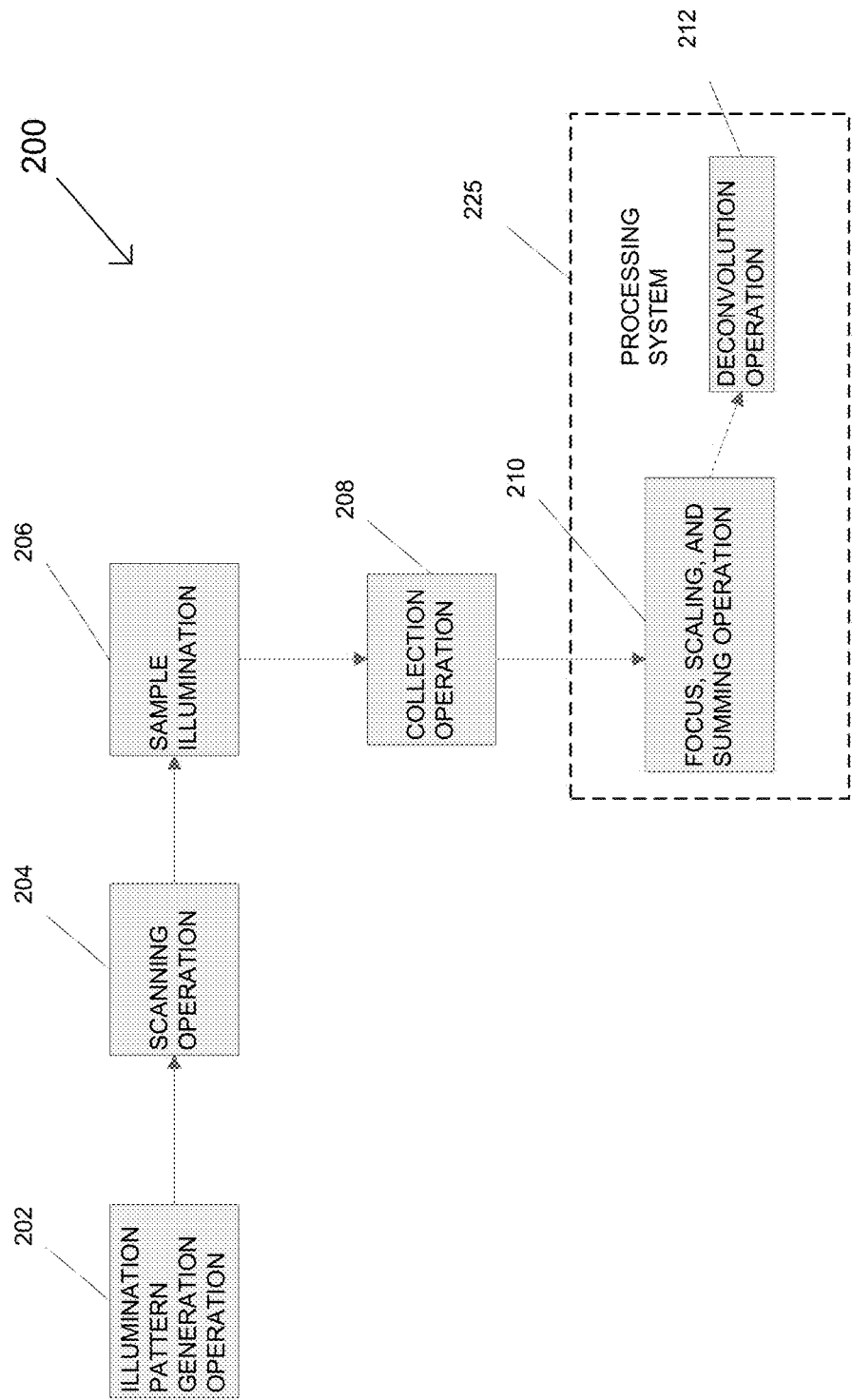
FIG. 2 is a simplified block diagram illustrating another method for generating a multi-focal pattern in another embodiment of the multi-focal SIM system.

Referring to FIG. 2, another method for generating multi-focal patterns according to another embodiment of the multi-focal SIM system, designated 200, is illustrated. Multi-focal SIM system 200 performs an illumination pattern generation operation 202, in which a single light beam is split into a plurality of light beams for generating one or more multi-focal patterns of the plurality of light beams. In a scanning operation 204, the plurality of light beams for each multi-focal pattern is rastered onto a sample 206. The sample 206 produces fluorescent emissions in response to the multi-focal patterns that are detected in a collection operation 208. In the collection operation 208 a detector collects the in-focus fluorescent emissions and transmits the collected data to a processing system that performs a processing operation 210. The processing operation 210 removes out-of-focus fluorescent emissions in each multi-focal pattern, scales the remaining in-focus fluorescent emissions, and then sums the scaled, in-focus fluorescent emissions to generate a composite image composed from the plurality of fluorescent emissions created by the multi-focal patterns. In some embodiments, the collected data may then undergo a deconvolution operation 212 similar to the deconvolution operation 118, which performs a de-blurring of the composite image to further enhance image resolution.

Figure 3:
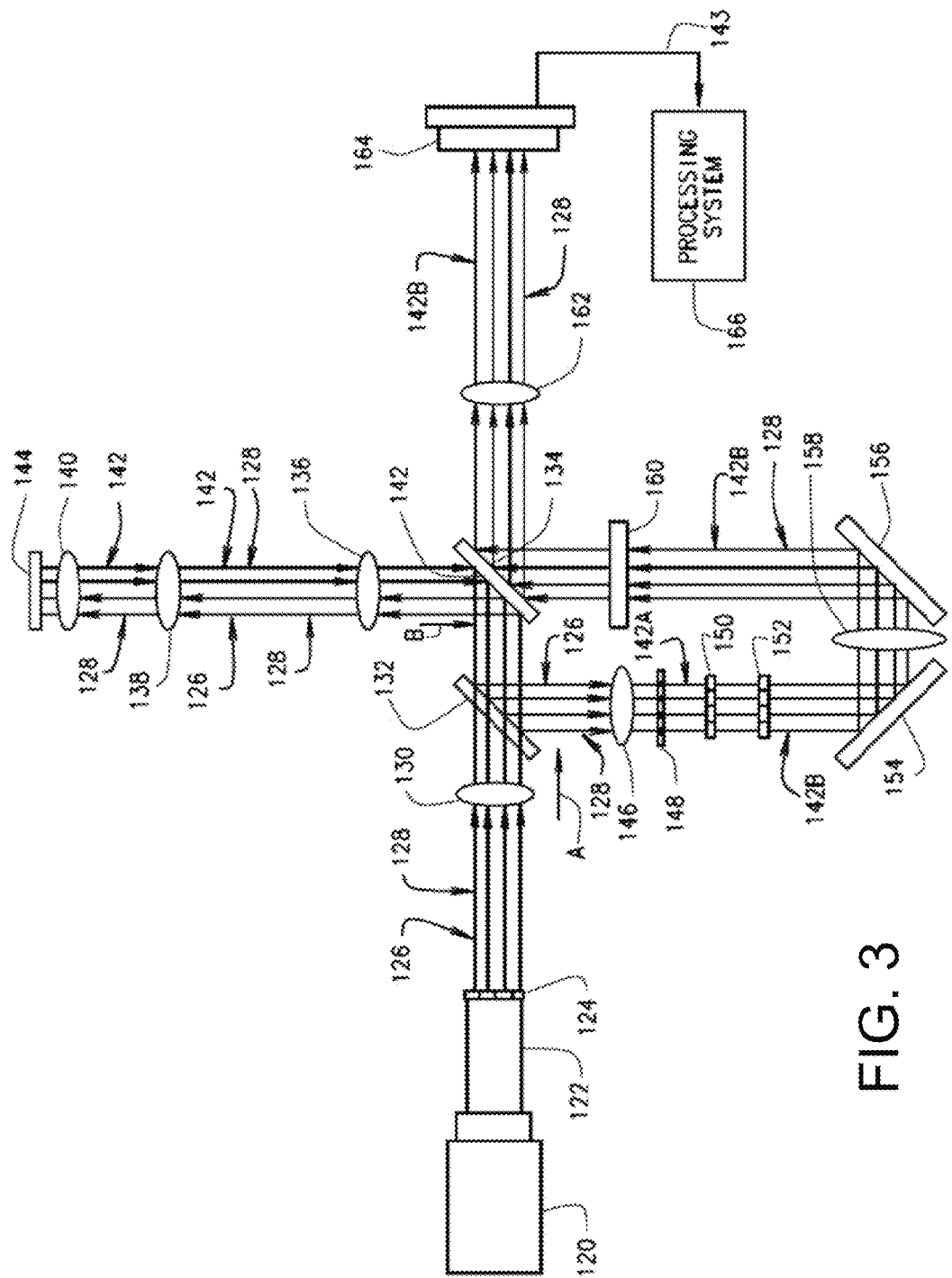
FIG. 3 is a simplified illustration showing the various components for one embodiment of the multi-focal SIM system of FIG. 1.

Referring to FIG. 3, one embodiment of the multi-focal SIM system 100 may include an illumination source 120, for example a laser, for generating a single light beam 122 that is transmitted through a beam splitter 124, such as a microlens array. The beam splitter 124 splits the single light beam 122 into a plurality of light beams 126 with each of the plurality of light beams 126 having a different focal point that collectively form a multi-focal pattern 128. In some embodiments, a first lens 130 images each multi-focal pattern 128 through a dichroic mirror 132 in direction A and onto a scanning apparatus 134, such as a galvanometer, to perform the scanning operation 104.

During the scanning operation 104, the scanning apparatus 134 rasters each multi-focal pattern 128 of the plurality of light beams 126 onto a sample 144 through an arrangement of a second lens 136, a tube lens 138 and an objective lens 140 and onto the sample 144.

In response to the sample 144 being illuminated by the multi-focal patterns 128 of the plurality of light beams 126, the sample 144 emits fluorescent emissions 142 caused by the multi-focal patterns 128 composed of light beams 126. The plurality of fluorescent emissions 142 for each multi-focal pattern 128 emitted by the illuminated sample 144 is then captured through the objective lens 140, and passed through the tube lens 138 and second lens 136 and onto the scanning apparatus 134, which de-scans each of the plurality of fluorescent emissions 142 by rastering the fluorescent emissions 142 from the second lens 136 and onto the dichroic mirror 132 in a direction B opposite that of direction A in which the plurality of light beams 126 pass directly through the dichroic mirror 132. In direction B, the plurality of fluorescent emissions 142 are redirected by the dichroic mirror 132 to pass through a third lens 146 in which the plurality of fluorescent emissions 142 are then focused onto a pinhole array 148 to perform the pinholing operation 110.

During the pinholing operation 110, the pinhole array 148 physically blocks and rejects out-of-focus fluorescent emissions 142 and allows only in-focus fluorescent emissions 142A to pass through the pinhole array 148. In one embodiment, the pinhole array 148 may include a plurality of apertures configured to permit only in-focus fluorescent emissions 142A to pass through the pinhole array 148, while blocking any fluorescent emissions 142 that do not pass through one of the apertures.

After passing through the pinhole array 148, the plurality of in-focus fluorescent emissions 142A are scaled using the scaling operation 112 discussed above that locally contracts each of the focal points for a respective multi-focal pattern 128 by a predetermined factor, for example a factor of two, using a first micro-lens array 150 arranged in series with a second micro-lens array 152. In one embodiment, the first micro-lens array 150 collimates the multi-focal pattern 128 of in-focus fluorescent emissions 142A, while the second micro-lens array 152 receives the collimated in-focus fluorescent emissions 142A and modifies the focal length for the collimated in-focus fluorescent emissions 142A such that each foci are scaled down by a predetermined factor to achieve local contraction of the multi-focal pattern 128. In some embodiments, the scaled in-focus fluorescent emissions 142B caused by each multi-focal pattern 128 are then redirected by a first mirror 154 to pass through a fourth lens 158 for focusing the scaled in-focus fluorescent emissions 142B onto a second mirror 156. The second mirror 156 redirects the scaled in-focus fluorescent emissions 142B to pass through an emission filter 160 that permits only scaled, in-focus fluorescent emissions 142B with a particular wavelength range, for example 515 nm, to pass through the emission filter 160. Once the scaled, in-focus fluorescent emissions 142B are filtered, the scanning apparatus 134 rasters the fluorescent emissions 142B onto the detector 164 through a fifth lens 162 such that the scaled, in-focus fluorescent emissions 142B for each multi-focal pattern 128 are collected and the in-focus fluorescent emissions 142B are summed by the detector 164 to produce a composite image 143. The process of collecting the fluorescent emissions 142B caused by multi-focal patterns 128 is repeated until the entire field of view has been illuminated and all the resulting fluorescent emissions 142B are collected by the detector 164.

In some embodiments, the detector 164 may be a camera with the shutter left open to exposure as the scaled, in-focus fluorescent emissions 142B are rastered onto the detector 164 for collection until the entire field of view is illuminated and all the collected data is received.

In some embodiments, the composite image 143 is transmitted to a processing system 166 that performs the deconvolution operation 118 that performs a de-blurring function to enhance the resolution of each composite image 143.

Figure 4:
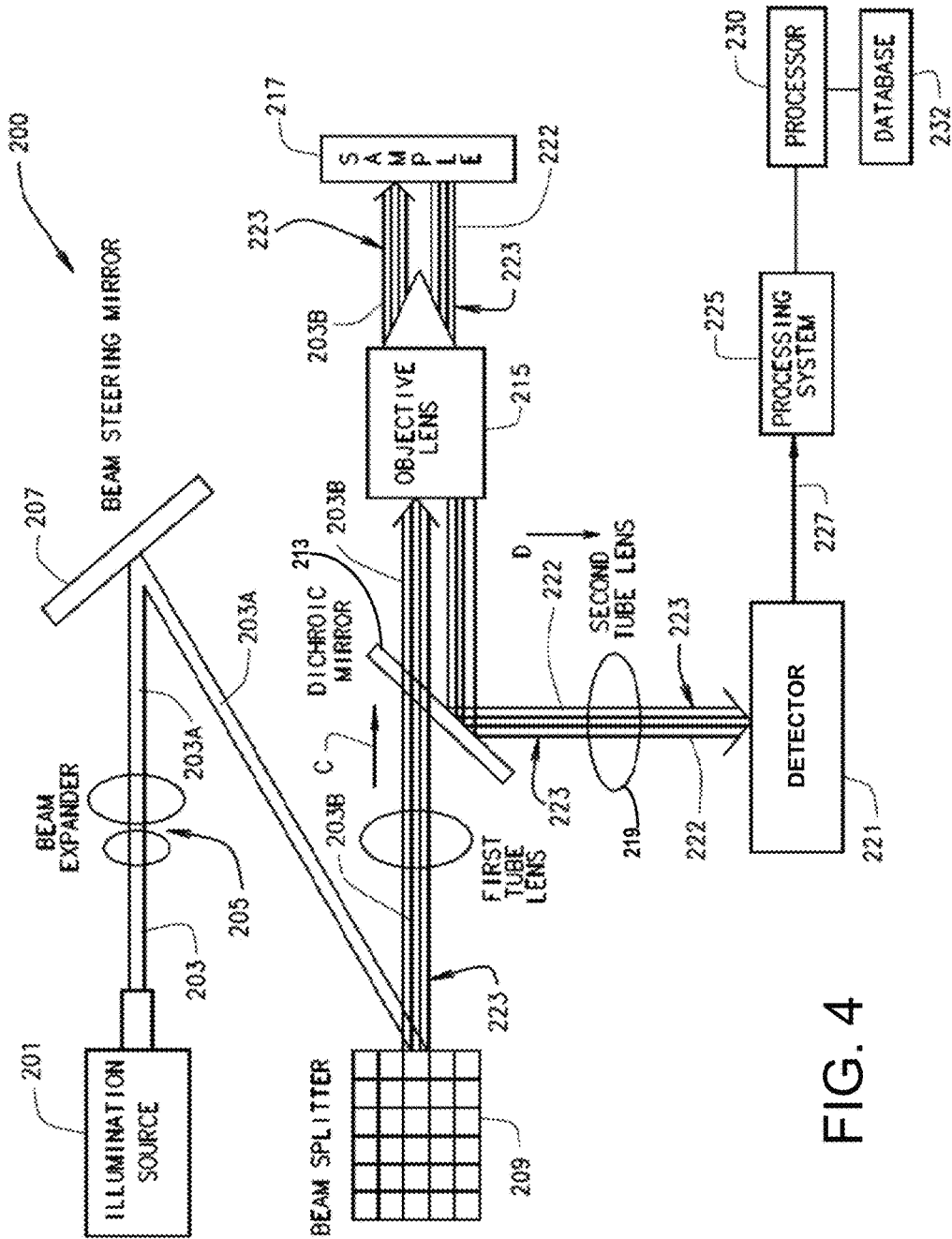
FIG. 4 is a simplified illustration showing the various components for one embodiment of the multi-focal SIM system of FIG. 2.
Figure 5:
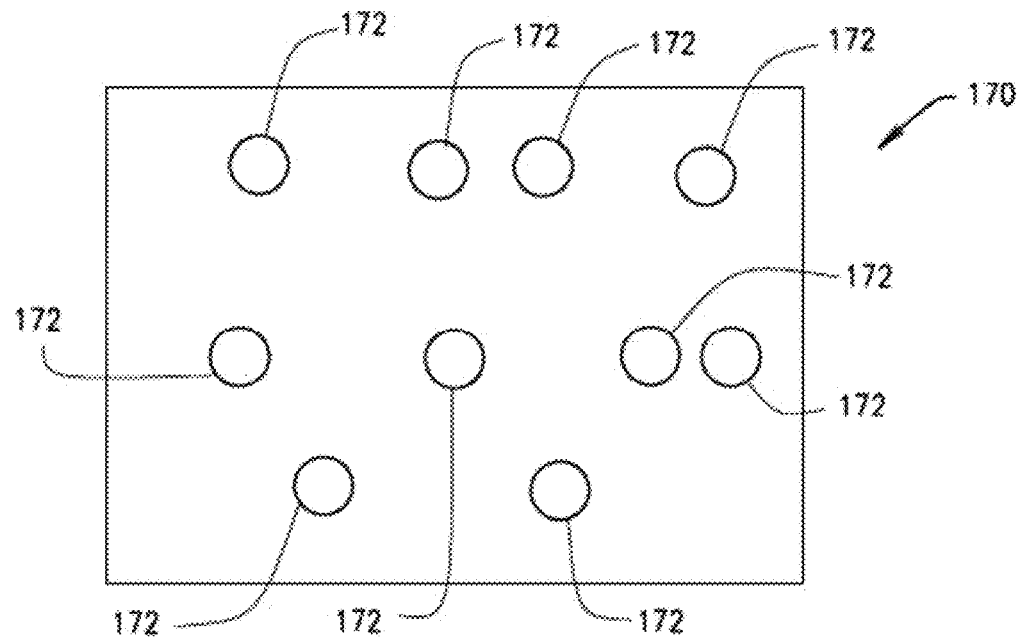
FIG. 5 is a simplified illustration showing a multi-focal pattern with a plurality of focal points.

Referring to FIG. 4, one embodiment of the multi-focal SIM system 200 for generating a multi-focal pattern 223 may include an illumination source 201 that generates a single light beam 203 that is transmitted through a beam expander 205 that produces an expanded single light beam 203, which is reflected off a beam steering mirror 207 for performing the scanning operation 204 that scans the expanded light beam 203 onto a beam splitter 209, for example a commercially available digital micromirror device (DMD) or a swept field confocal unit. In some embodiments, the DMD generates and switches multi-focal patterns 223 with each focal point being an illuminated spot on the multi-focal pattern 223. Each illumination spot is created by a single DMD mirror pixel being in the ON position such that a portion of the expanded light beam 203 is reflected off the single DMD mirror pixel. The beam splitter 209 performs the illumination pattern generation operation 202 that splits the expanded light beam 203 being scanned into a plurality of expanded light beams 203A that collectively form a sequence of multi-focal patterns 223. The plurality of expanded light beams 203A for each multi-focal pattern 223 is passed through a first tube lens 211 to pass directly through a dichroic mirror 213 along a direction C.

After passing directly through the dichroic mirror 213 the expanded light beams 203A are focused by an objective lens 215 onto a sample plane for performing sample illumination 206 of sample 217 and generate a plurality of fluorescence emissions 222 emitted by the sample 217. In the collection operation 208, the fluorescent emissions 222 are focused back through the objective lens 215 and onto the dichroic mirror 213 along direction D perpendicular to that of direction C such that the fluorescent emissions 222 for each multi-focal pattern 223 are redirected and pass through a second tube lens 219. The second tube lens 219 focuses the fluorescent emissions 222 onto a detector 221, thus collecting each multi-focal pattern 223 in the form of collected data 227 for transmission to a processing system 225 that rejects out-of-focus light and performs scaling and summing operation 210. The process of collecting the fluorescent emissions 222 caused by each multi-focal pattern is repeated until the entire field of view has been illuminated. In some embodiments, the processing system 225 may include a processor 230 in operative communication with the detector 221 for processing collected data 227 stored in a database 232, such as a computer-readable medium, by executing instructions a shall be discussed in greater detail below.

Figure 7:
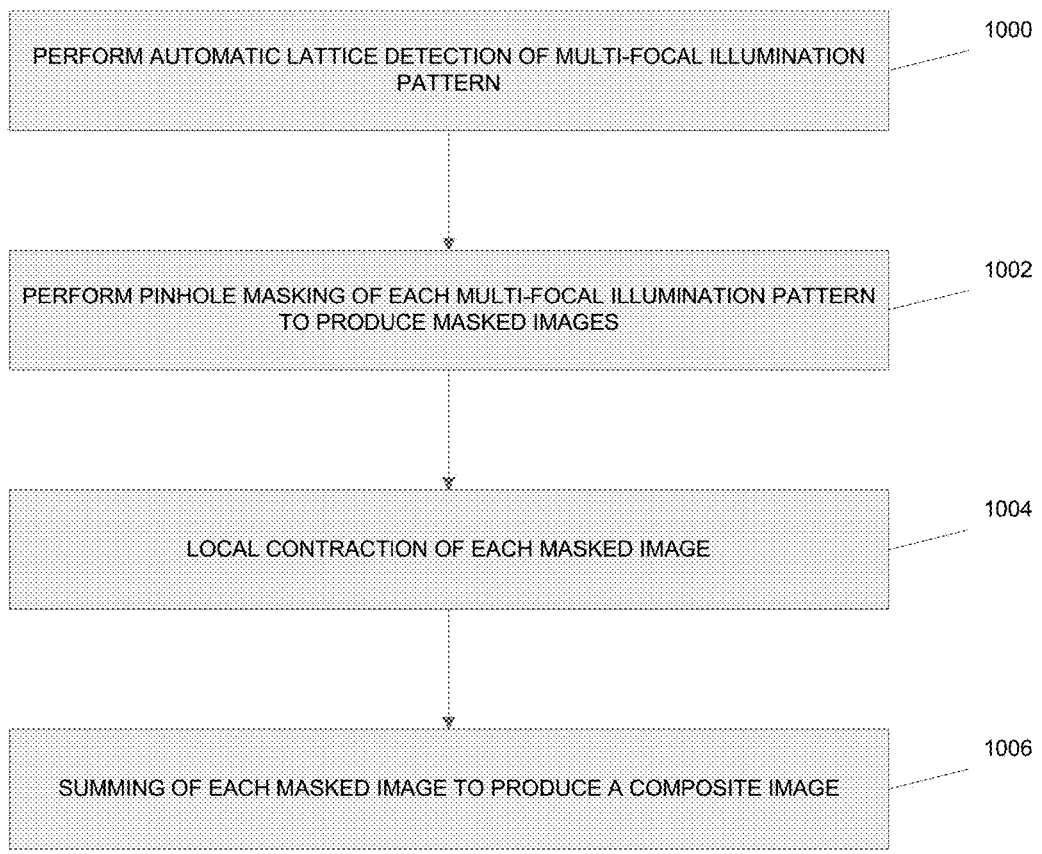
FIG. 7 is a flow chart illustrating one method for conducting a, scaling and summing operation by a processing system in the multi-focal SIM system of FIG. 4.

In one embodiment, the processing system 225 rejects out-of-focus fluorescent emissions 222, and performs the scaling and summing operation 210 on the collected data 227 for each multi-focal pattern 223 using a computerized procedure for processing the collected data 227. Referring to FIG. 7, a flow chart illustrates one method for performing the out-of-focus fluorescence rejection, scaling and summing operation 210 using the processing system 225. At block 1000, the processing system 225 performs an automatic lattice detection of the multi-focal illumination pattern 223. Specifically, automatic lattice detection determines the position of each illumination focal point for a particular multi-focal pattern 223 in order to perform pinhole masking and local contraction of the various fluorescent foci. For example, the automatic lattice detection determines five vectors to completely specify the location of all focal points for each fluorescent emission 222 in a particular multi-focal pattern 223 in an image acquisition series. In some embodiments, the five vectors may be lattice vectors, shift vectors and an offset vector. Two lattice vectors specify the two-dimensional displacement between any two neighboring illumination spots (e.g., focal points). As such, any lattice point displaced by a lattice vector will fall on another lattice point. Due to thermal shift, the exact locations of each illumination spot may vary in time, so accurately extracting all vectors for each measured dataset from the collected data 227 provides the best results using the following methodology.

Figure 8:
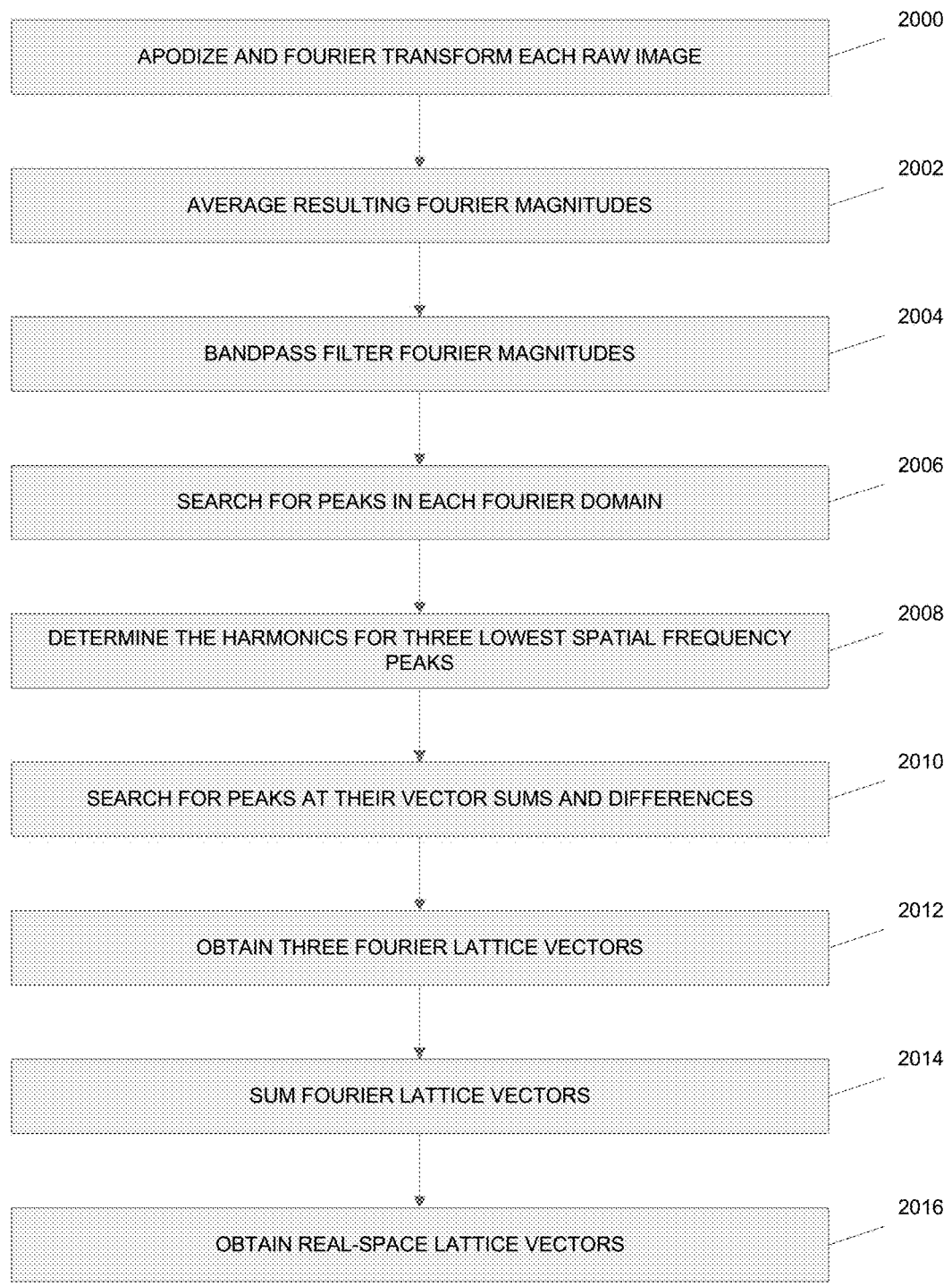
FIG. 8 is a flow chart illustrating one method for obtaining lattice vectors when executing the out-of-focus fluorescence rejection, scaling and summing operation of the processing system.

Referring to FIG. 8, a method for accurately extracting all vectors for each measured dataset of collected data 227 is shown when the processing system 225 performs the out-of-focus rejection, scaling and summing operation 210. The offset vector specifies the absolute position of the illumination spot closest to the center of a multi-focal pattern in any one image acquisition series being processed by the processing system 225. The shift vectors specify the distance of each illumination spot for a particular multi-focal pattern 223 moves between consecutive images. Since the multi-focal pattern 223 is rastered in a two-dimensional plane, a "fast" shift vector is applied at every step of the operation 210 and a "slow" shift vector is applied when a "fast" shift vector has completed illuminating one row. As used herein, the term "fast" shift vector specifies those lattice points in a single row and the term "slow" shift vector specifies successive rows. At block 2000, each raw image representing the fluorescence 142B captured from a particular multi-focal pattern 223 is multiplied by a Hann window (which prevents ringing in the Fourier domain) and Fourier transformed. At block 2002, the resulting Fourier magnitudes are averaged to obtain a high signal-to-noise measurement of peak locations in the Fourier space. At block 2004, the averaged resulting Fourier magnitudes are filtered through a bandpass filter. At block 2006, a search for spikes or peaks in the Fourier domain is accomplished. Since the raw images for summed Fourier magnitudes are expected to be a periodic lattice of peaks, the dimensions of each periodic lattice is made by determining the local Fourier maxima, which are either lattice elements or noise. At block 2008, the harmonics for the three lowest spatial frequency peaks are determined by computationally searching for peak intensities at and near the expected frequency multiples. At block 2010, given the locations of the three lowest spatial frequency peaks with harmonics, a search is conducted for peaks at their vector sums and differences, which compose the lattice vectors. In the present method, the peaks in a periodic lattice predict the location of other peaks in the same lattice with every lattice point being located at the vector sum of an integer number of Fourier lattice vectors. At block 2012, the processing system 225 solves the resulting system of equations by linear squares to obtain three lattice vectors. Any single peak in the Fourier domain will have some positional error due to noise or pixelization. Utilizing the method of least squares, the information provided by each peak produces a more accurate measurement of the lattice dimensions. At block 2014, the processing system 225 sums the lattice vectors to determine an error vector and then subtracts one-third of the error vector from each Fourier lattice vector. At block 2016, any two of the two Fourier lattice vectors are selected and transformed to obtain real space lattice vectors. It has been discovered that obtaining two lattice vectors for the multi-focal illumination pattern makes it substantially easier to measure the offset vector and the shift vector.

Figure 9:
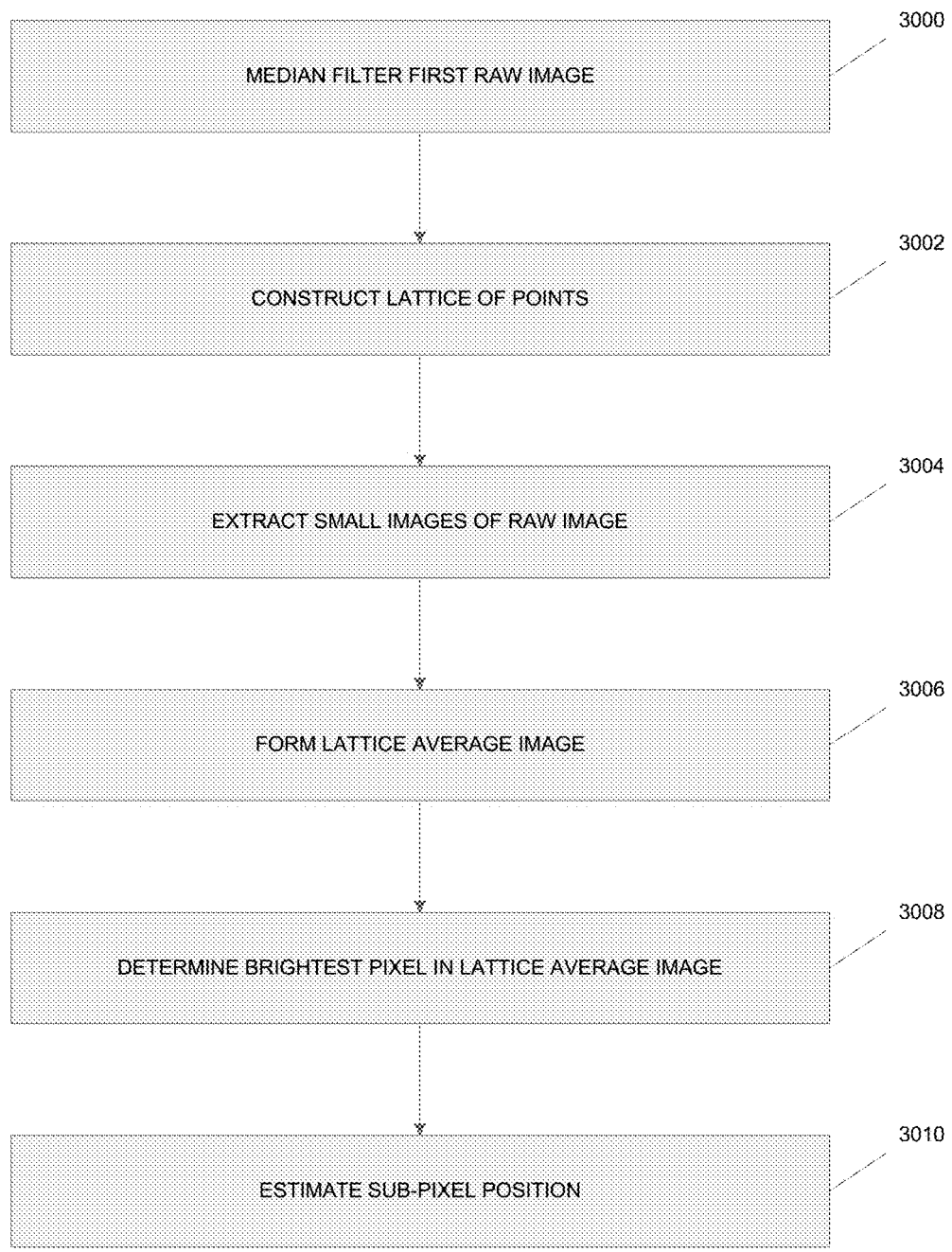
FIG. 9 is a flow chart illustrating one method for obtaining offset vectors when executing the out-of-focus fluorescence rejection, scaling and summing operation of the processing system.

Referring to FIG. 9, a method for determining offset vectors is shown when the processing system 225 performs the rejection of out-of-focus blur, scaling and summing operation 210. At block 3000, a first raw image is median filtered. At block 3002, a lattice of points from the measured lattice vectors is constructed with an offset vector of zero. At block 3004, a set of smaller images centered at each lattice point is extracted from the median-filtered raw image using interpolation for sub-pixel centering. At block 3006, the smaller images are averaged to form a "lattice average" image. At block 3008, the brightest pixel in the lattice average image is determined. At block 3010, the sub-pixel position of each intensity peak in the lattice average image is estimated using interpolation techniques.

Figure 10:
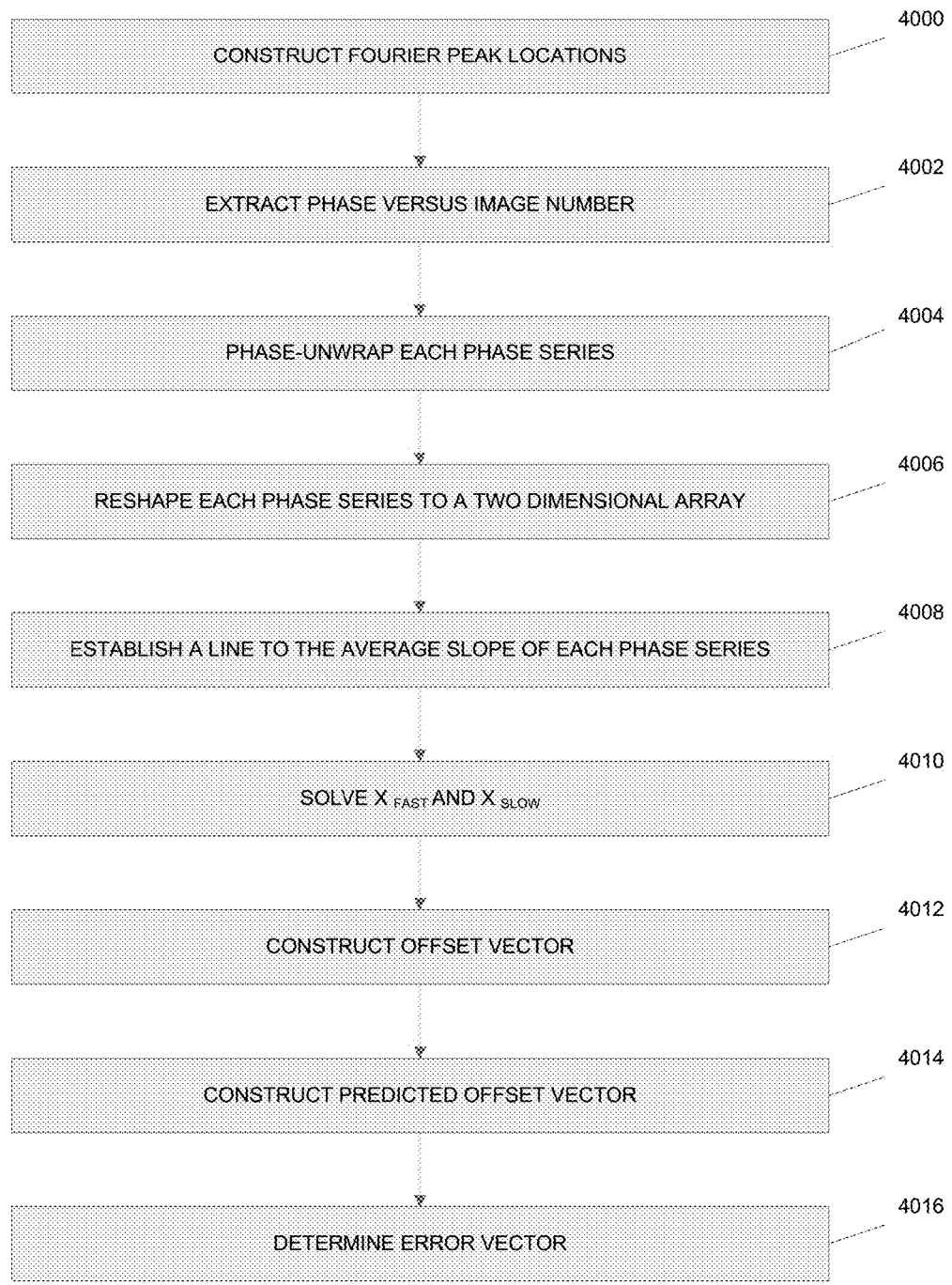
FIG. 10 is a flow chart illustrating one method for obtaining shift vectors executing the out-of-focus fluorescence rejection, scaling and summing operations of the processing system.

Referring to FIG. 10, a method for determining the shift vectors is shown when the processing system 225 performs the rejection of out-of-focus blur, scaling and summing operation 210. At block 4000, a set of expected Fourier peak locations is constructed from the measured Fourier lattice vectors. At block 4002, extract phase is extracted for each image number for the transformed collected data 227. At block 4004, the processing system 525 phase-unwraps each series of multi-focal patterns 223 to remove $2\pi$ jumps. It has been noted that the magnitude of the Fourier transform of each raw image is independent of shifts of the raw images. Information about shifting is encoded in the phase of the Fourier transforms. At block 4006, the processing system 225 reshapes each phase series in two-dimensional series to a two-dimensional array with the same dimensions as the scan pattern (e.g., 16 pixels×14 pixels). After reshaping of each phase series, at block 4008, a line is fit to the average slope of each phase series in both the "fast" and "slow" directions. In each consecutive raw image that is detected, the illumination shifts by $X_{FAST}$. At the end of each row, the illumination also shifts by $X_{SLOW}$. If a raw image shifts by X, the phase of a peak in the Fourier space located at k shifts by k*X. At block 4010, the processing system 225 solves the resulting system of equations for $X_{FAST}$ and $X_{SLOW}$. At block 4012, an offset vector is constructed for the first and last frames of the series of multi-focal patterns 223. Computing the offset vector for the last frame, which uses the same process that computed the offset vector of the first frame, provides a strong constraint that greatly increases the accuracy of the estimate. At block 4014, a predicted offset vector is constructed based on the current estimate for $X_{FAST}$ and $X_{SLOW}$. Once the predicted offset vector is constructed, the difference between the two vectors is determined to be an error vector, which is divided by the number of raw images in the scan, and subtracted from $X_{SLOW}$.

Figure 11:
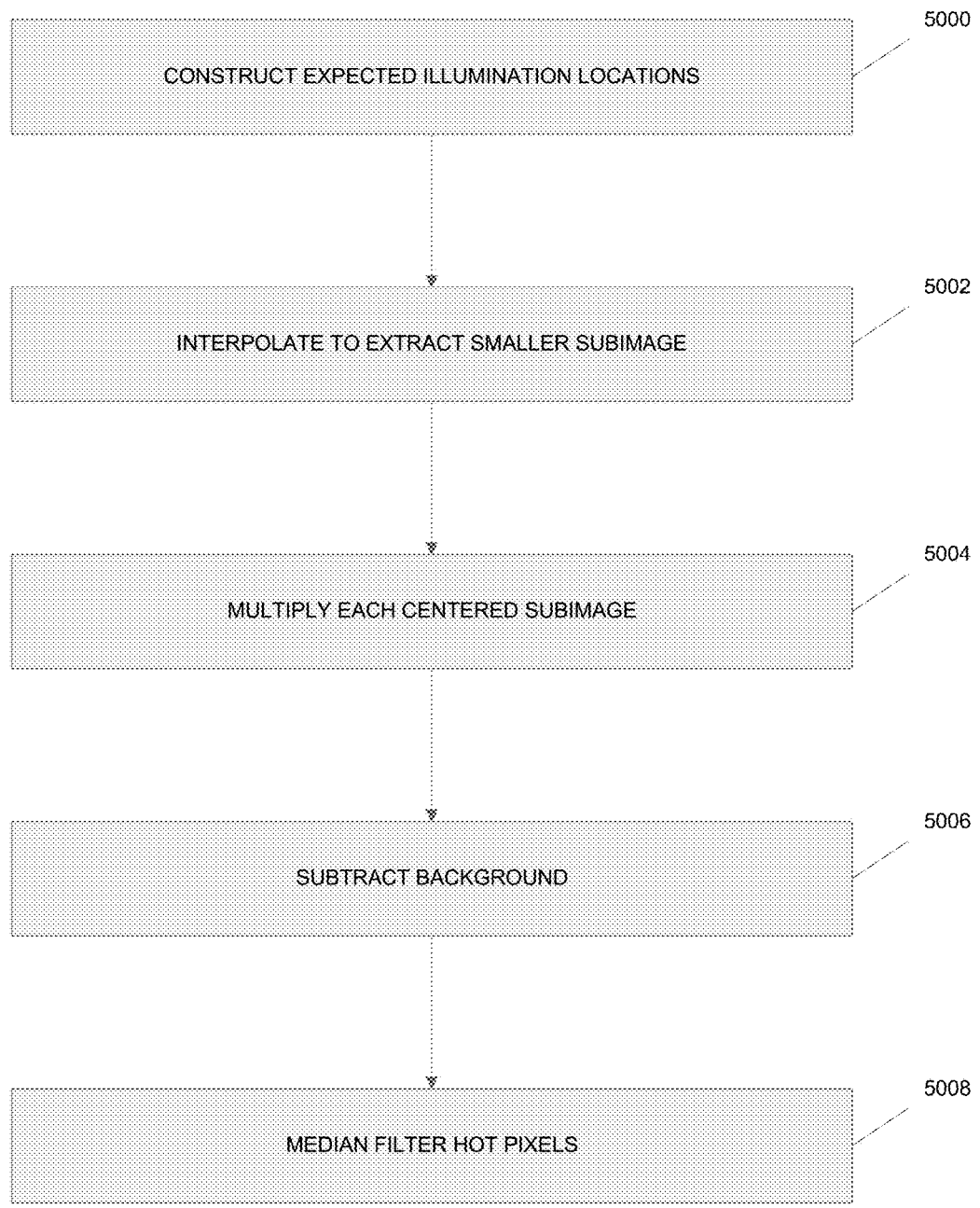
FIG. 11 is a flow chart illustrating one method for pinhole masking when executing the out-of-focus fluorescence rejection, scaling and summing operation of the processing system.

Referring to FIG. 11, a method for pinhole masking is shown for rejecting out-of-focus blur when the processing system 225 performs the out-of-focus blur, scaling and summing operation 210. At block 5000, a set of expected illumination locations based on the vectors determined above is constructed for each raw image collected during the collection operation 208. At block 5002, smaller subimages centered at each illumination location are extracted using interpolation techniques and then at block 5004 each centered subimage is multiplied by the processing system 525 by a two-dimensional Gaussian mask. These process steps simulate the effect of physical pinholes. At block 5006, the background may be optionally subtracted from each subimage and the centered subimage multiplied by a correction factor given by calibration data. At block 5008, individual hot pixels may be optionally median filtered by the processing system 525.

Figure 12:
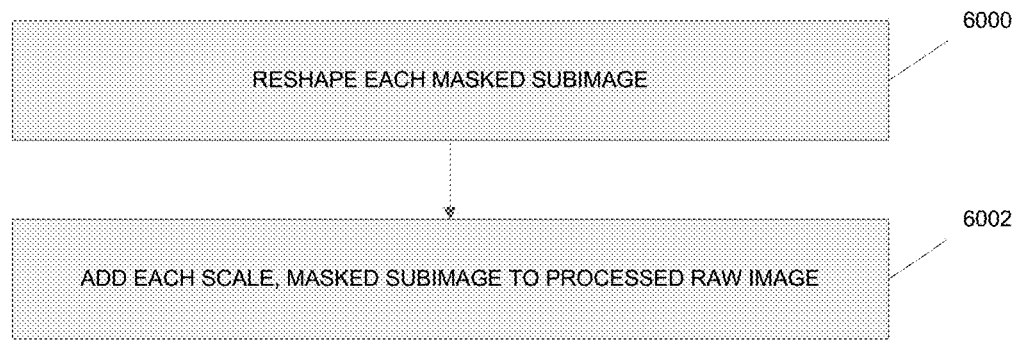
FIG. 12 is a flow chart illustrating one method for scaling and local contraction when executing the out-of-focus fluorescence rejection, scaling and summing operation of the processing system.

Referring to FIG. 12, a method for scaling and performing local contraction is shown when the processing system 225 performs the rejection of out-of-focus blur, scaling and summing operation 210. At block 6000, each masked subimage is re-sampled to shrink the masked subimage by a factor of about two. At block 6002, each scaled, masked subimage is added to the processing raw image.

Figure 13:
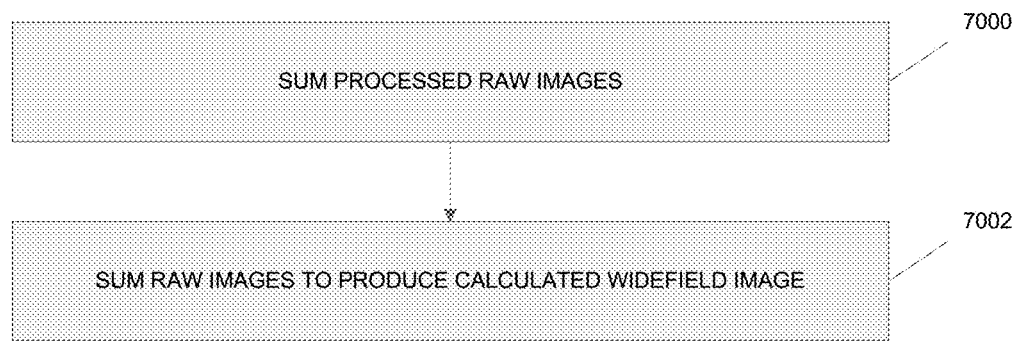
FIG. 13 is a flow chart illustrating one method for summing when executing the out-of-focus fluorescence rejection, scaling and summing operation of the processing system.

Referring to FIG. 13, a method for summing is shown when the processing system 225 performs the rejection of out-of-focus blur, scaling and summing operation 210. At block 7000, the processed raw images are summed to form a composite image. At block 7002, the raw images may be optionally summed to produce a calculated "widefield" image.

The resulting composite image produced by the rejection of out-of-focus blur, scaling and summing operation 210 has been shown to have a $\sqrt{2}$ better resolution than a typical widefield image produced by a conventional widefield microscopy. The rejection of out-of-focus blur, scaling and summing operation 210 also greatly improves optical sectioning, similar to a conventional spinning-disk or swept-field confocal microscope.

Testing

To investigate the potential of the multi-focal SIM system 200 for biological imaging, antibody-labeled microtubules in human osteosarcoma (U2OS) cells embedded in fluoromount were imaged. The following is a description of the illumination system (FIG. 14), microscope system, sample preparation, and data processing of captured images. The use of multi-focal patterns in combination with deconvolution allowed us to investigate a variety of samples at imaging rates of 1 Hz, at resolutions down to 145 nm laterally and 400 nm axially. Compared to conventional structured illumination microscopy systems, the multi-focal SIM system 200 provided three-dimensional images of samples 5-8 times thicker than conventional structured illumination microscopy systems. In the present investigation, microtubules were imaged in live transgenic aebrafish embryos at depths grater than 45 μm from the coverslip surface. In addition, four-dimensional SIM datasets of GFP-labeled histones in live nematode embryos were obtained.

For testing, a periodic lattice of approximately equilateral triangles for our illumination point locations because this particular pattern maximized the distance between any two nearest neighbors for a given density of points, thereby minimizing crosstalk. The multi-focal illumination pattern was translated one Digital Micromirror Device (DMD) pixel at a time, which corresponded to a step size of 120 nm in the sample plane. Larger steps did not evenly illuminate the sample, giving a visible striping artifact, while smaller steps increased acquisition time and dose with no increase in image quality.

Multi-focal patterns were imaged onto the sample, which was mounted on a commercial inverted microscope, and a scientific-grade complementary metal-oxide-semiconductor camera (sCMOS) was used to record one raw image for each multi-focal pattern position. By varying the spacing between the illumination points, acquisition speed may be traded for sectioning quality. It was discovered that widely spaced foci had less crosstalk, but additional multi-focal illumination patterns were required to evenly illuminate a sample. In contrast, denser foci had more crosstalk, but required correspondingly fewer multi-focal patterns to evenly illuminate the sample. It was found that a multi-focal pattern with a 16 pixel horizontal and a 14 pixel vertical separation between scan points provided good results in the biological samples investigated. The resulting 224 raw exposures taken at 222 Hz for a 480 pixel×480 pixel field of view corresponded to about a 1 Hz super-resolution image acquisition rate.

Figure 15A:
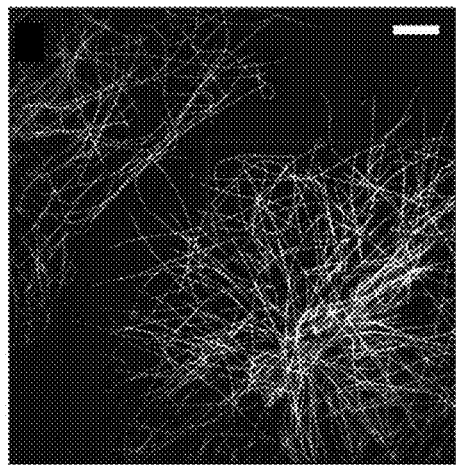
FIGS. 15A-15C illustrate various images of a sample embedded in fluoromount and FIG. 15D is a graphical representation showing the normalized intensity of the sample.
Figure 15B:
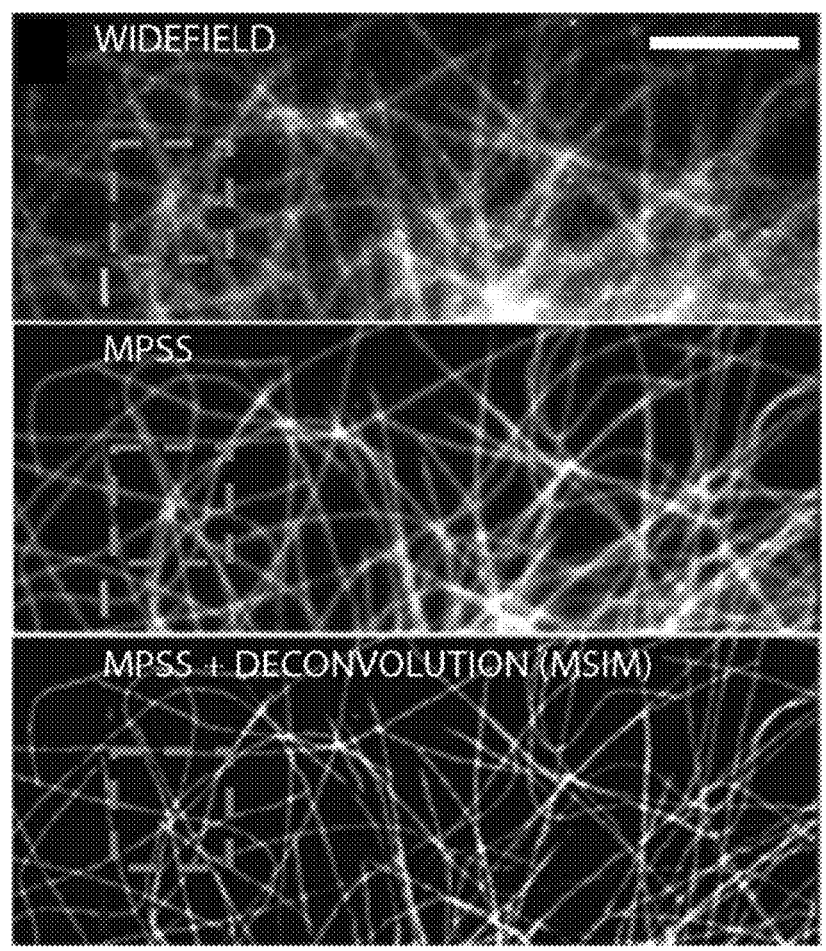
Figure 15C:
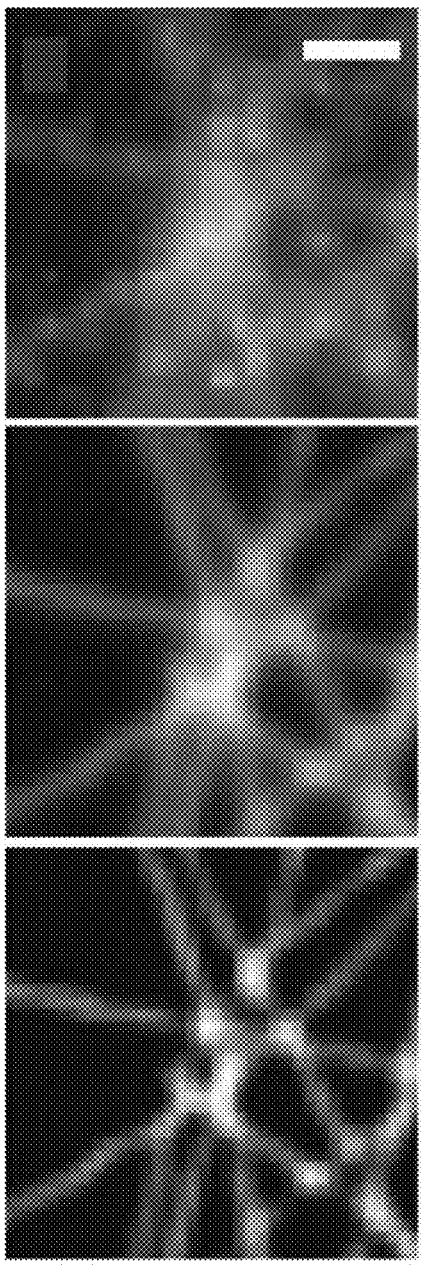
Figure 15D:
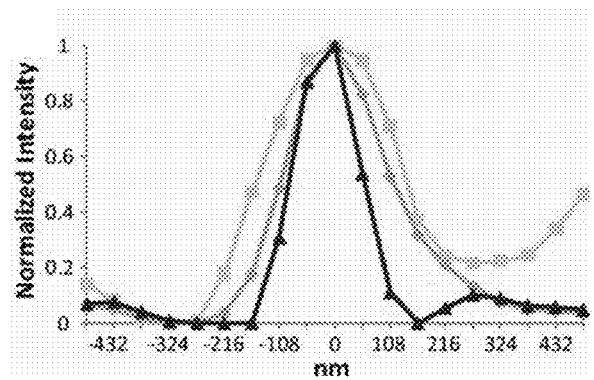

To investigate the potential of multi-focal SIM system 200 for biological imaging, we imaged antibody-labeled microtubules in human osteosarcoma (U2OS) cells embedded in fluoromount as shown in the images illustrated in FIGS. 15A-15C. Compared to widefield images, the multi-focal illuminated, pinholed, summed, and scaled images produced by the SIM system 200 improved image resolution including image contrast. In addition, parallel, iterative deconvolution further improved the resulting composite image, which revealed features previously obscured by diffraction. The apparent full-width at half maximum (FWHM) intensity of microtubules in multi-focal SIM system 200 images was 145 nm as shown in FIG. 15D, which was a two-fold improvement compared to widefield imaging. Similar experiments on 110 nm subdiffractive beads confirmed this result (multi-focal SIM system 200 FWHM 146+/−15 nm vs. widefield FWHM 284+/−32 nm, N=80 beads. The total acquisition time for the 48 μm×49 μm field was about 1 s, a 6500-fold improvement over a conventional image scanning microscopy (ISM) system assuming the same 222 Hz raw frame rate for each microscopy system.

Figure 16A:
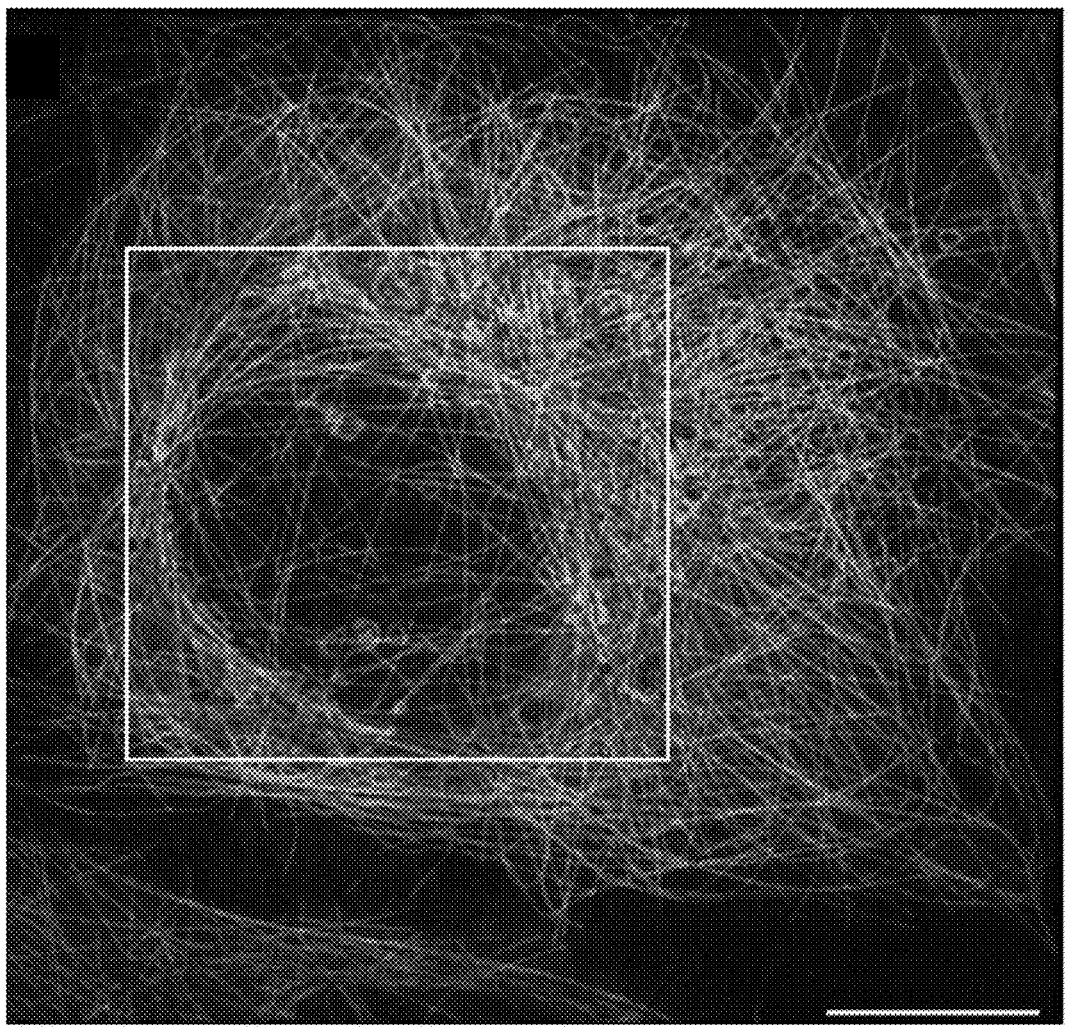
FIGS. 16A and 16B illustrate various images of dual-labeled three-dimensional samples embedded in fluoromount.
Figure 16B:
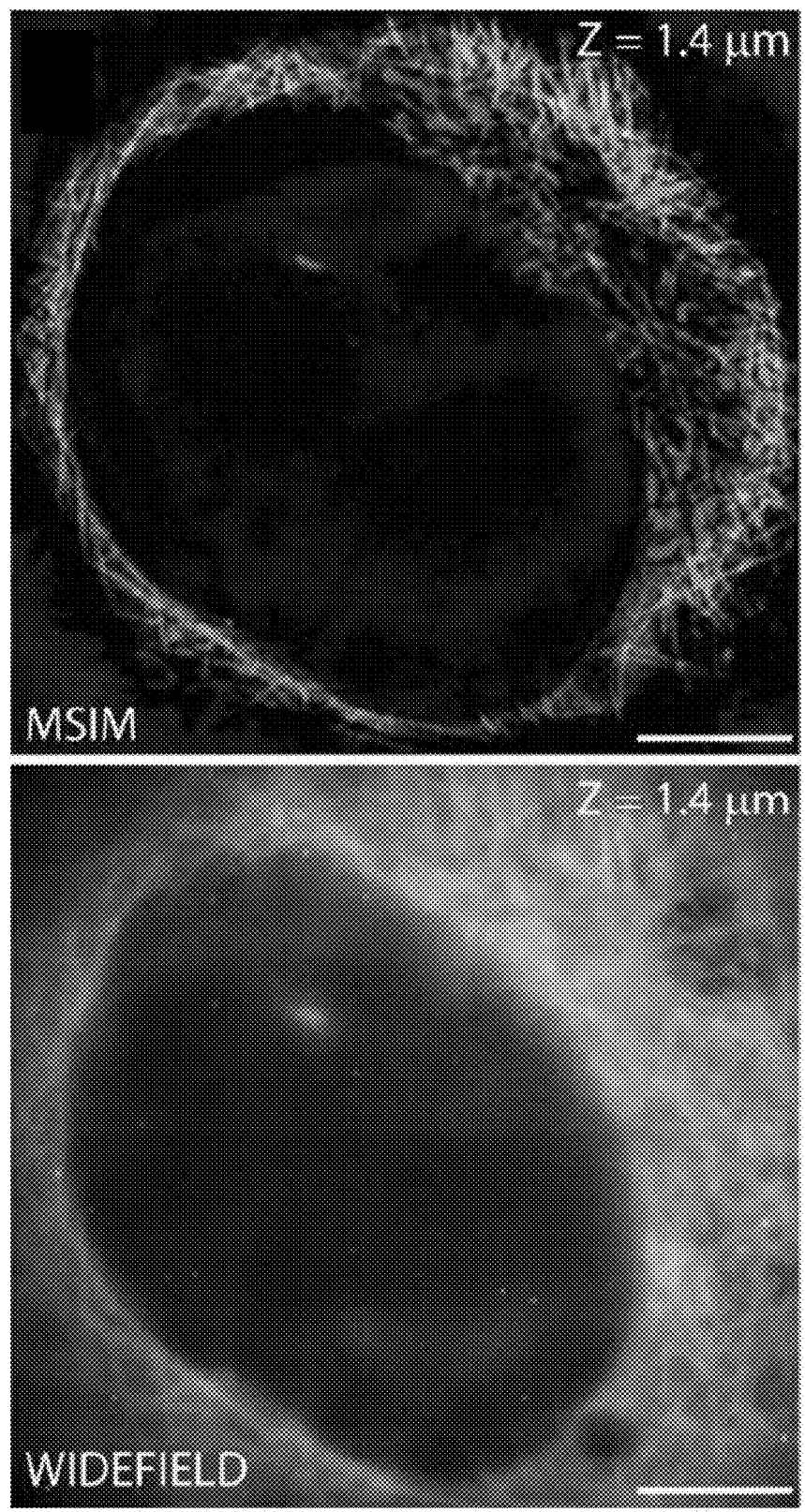
Figure 17A:
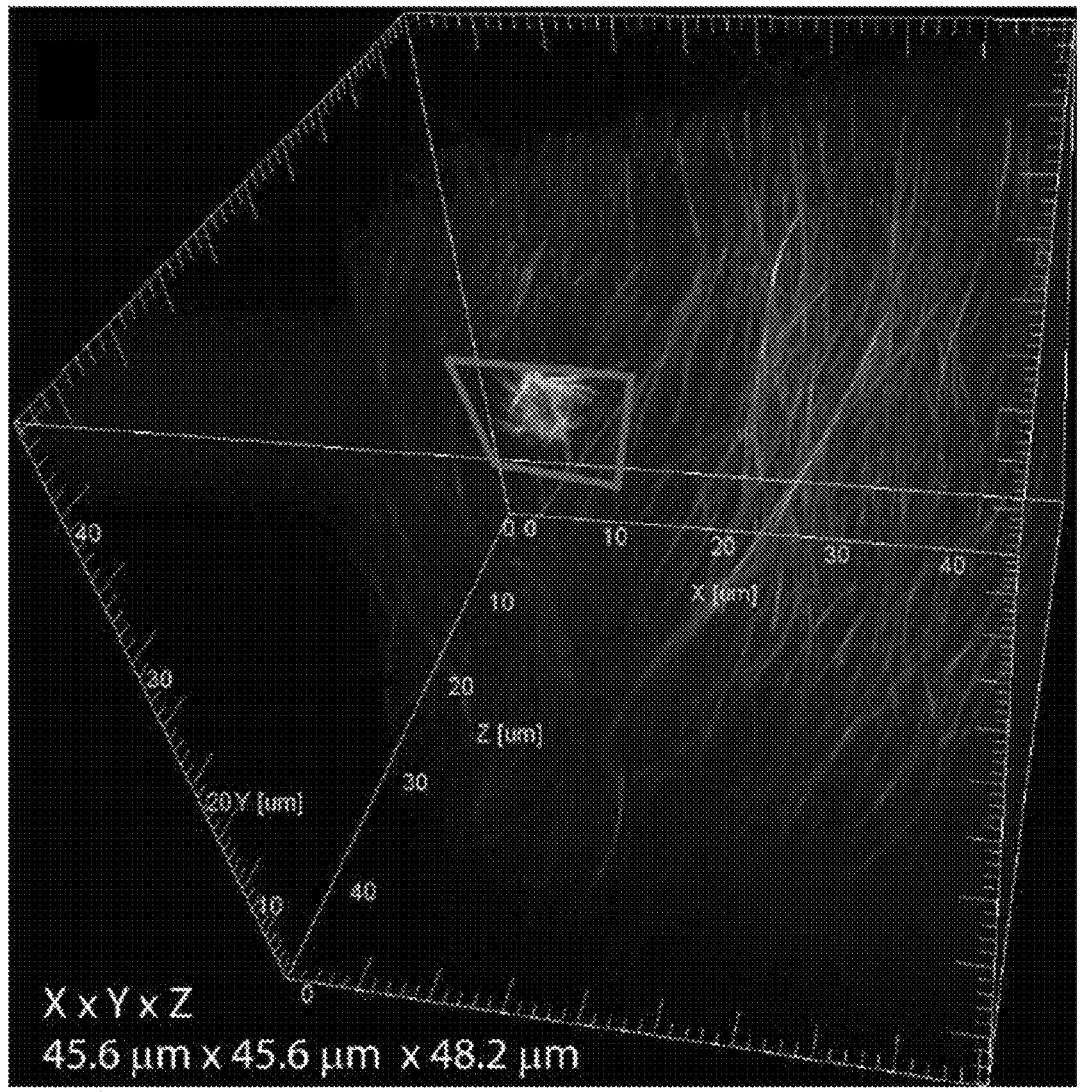

The suitability of the multi-focal SIM system 200 for dual-labeled, three-dimensional samples was also investigated as shown in the samples illustrated in FIGS. 16A and 16B. A Z stack of images on a fixed cell embedded in fluoromount was used. Immuno-labeled microtubules with Alexa Fluor 488 and stained mitochondria with Mitotracker Red obtained a volume of 3.7 μm thickness, with individual slices separated by 100 nm. Compared to widefield images obtained with the same total illumination dose, three-dimensional multi-focal SIM system 200 images provided a striking increase in image contrast, due to the combined physical (via digital pinholes) and computational (via three-dimensional deconvolution) removal of out-of-focus light.

The resulting composite images produced by the multi-focal SIM system 200 had approximately a two-fold resolution improvement over widefield imaging; better resolving microtubules and "worm-like" mitochondria. For example, better resolving of sub-diffractive voids at the ends of individual mitochondria was achieved including microtubule pairs separated by greater than 200 nm. Unexpectedly, multi-focal SIM system 200 also improved the axial resolution approximately two-times over widefield images, as microtututbules had apparent axial FWHM of about 400 nm. This result was confirmed on 100 nm subdiffractive beads (Multi-focal SIM system FWHM 402+/−49 nm; widefield 826+/−83 nm, N=80 beads.

The multi-focal SIM system 200 was also applied to three-dimensional imaging of thicker live samples in which the pinhole operation physically rejects out-of-focus light that would otherwise swamp the in-focus light signal. To demonstrate this capability, live, immobilized zebrafish embryos expressing a GFP transgene that labeled microtubules were imaged.

Using multi-focal illumination in accordance with the multi-focal SIM system 200, 241 slices were acquired spaced 0.2 μm apart at a two-dimensional imaging rate of 1 Hz. After pinhole focusing, scaling, and three-dimensional deconvolution, a volume of 48.2 μm thickness was achieved as shown in the images of the sample illustrated in FIGS. 17A-17D. Structural features such as the boundary between two adjacent somites, alignment of microtubules along the somite boundary, and microtubule free-regions corresponding to the nuclei of the developing muscle cells are clearly visible in the stack. Estimation of the z-position of successively deeper nuclei within this stack suggests that the imaging volume contained 6-7 cell layers.

In one test, the imaging rate of the multi-focal SIM system 200 captured a dividing cell in the epidermis without significant motion blur in the images. The resolution enhancement of multi-focal SIM system 200 was retained throughout the volume, as the separation between microtubule pairs at the site of the cell division was resolved to better than 200 nm, and microtubules in the epidermis had lateral FWHM 175+/−33 nm laterally (N=30) and 496+/−65 nm axially (N=21).

Illumination System

Figure 14:
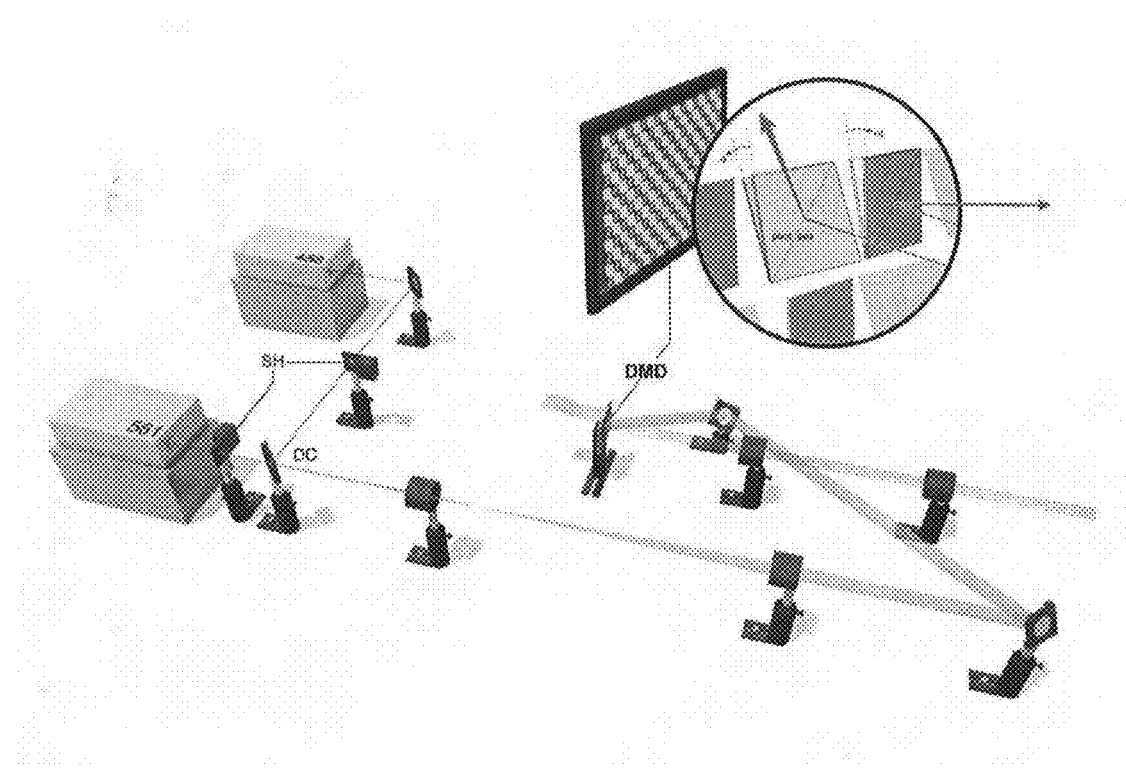
FIG. 14 is a simplified illustration showing the illumination system used during testing of one embodiment of the multi-focal SIM system.

In the illumination system, all optics were mounted on an optical table (Kinetic Systems, Vibraplane Model #5704-3660-23SPL) to minimize mechanical vibrations. For exciting fluorescence, two lasers were used: a 150 mW, 561 nm laser (561, Coherent, Sapphire 561-150 CW CDRH) and a 200 mW, 488 nm laser (488, Coherent, Sapphire 488-200 CDRH). Mechanical shutters (Thorlabs, SH05 and SC10) placed after each laser was used to control illumination. Beams were combined with a dichroic mirror (DC, Chroma, 525dcxru) and expanded 6.7 times with a beam expander constructed from two achromatic lenses (Edmund, f=30 mm, NT49-352-INK and Thorlabs, f=200 mm, AC254-200-A-ML0. Expanded beams were directed onto a digital micromirror device (DMD, Digital Light Innovations, D4100 DLP 0.55" XGA) 24 degrees off normal, so that in the ON position the micromirrors tilted the output beam normal to the DMD face. The center order of the resulting illumination pattern was demagnified 1.5 times with a beam de-expander (Thorlabs, f=75 mm, AC254-075-A-ML and f=50 mm, AC254-050-A-ML0, aligned in a 4f configuration such that the DMD face was re-imaged at the back focal plane of a 180 mm tube lens internal to the microscope (Olympus, IX-81). These elements are shown in FIG. 14. After entering the left side port of the microscope, the beam sequentially passed through (i) the tube lens; (ii) a dichroic mirror (Chroma, zt405/488/561); (iii) a 60× objective (Olympus, PlanApo, NA 1.45 TIRF, for single cells, or UPLSAPO 60XS, NA 1.3, for zebrafish and worm embryos) for a total demagnification of 90× between the DMD and the sample being illuminated. The illumination at the sample covered a circular region approximately 50 µm in diameter.

Microscope System

Structured illumination microscopy (SIM) imaging was performed on an Olympus IX81 inverted microscope equipped with both left and right side ports, and an automated XY stage with an additional Z piezoelectric stage (200 µm range, Applied Scientific Instrumentation, PZ-2000). The patterned excitation (e.g. multi-focal illumination pattern) created by the DMD was brought in via the left side port to the microscope. Fluorescence emitted by the illuminated sample was collected by the objective, reflected with a dichroic mirror (Chroma, zt405/488/561), passed through a 180 nm tube lens internal to the microscope, filtered appropriately to reject pump light (Semrock, LP02-488RE-25 and NF03-561E-25), and detected with a scientific-grade complementary metal-oxide-semiconductor (sCMOS) camera (Cooke, pco.edge) mounted on the right side port. Correctly aligning the sCMOS along the optical axis was critical in achieving near diffraction-limited performance. To aid in the correct positioning of the camera, a 60× objectives typically used in imaging with a 10× air objective (Olympus, CPlanFl 10×, 0.3NA), an optic much more sensitive to errors in axial alignment. A fixed illumination pattern (similar to one used in SIM) onto the fluorescent lake sample, and translated the camera along the optical axis until the apparent size of each illumination spot was minimized.

Sample Preparation

U2OS cells were cultured on ethanol sterilized, cleaned #1.5 25 mm diameter coverslips (Warner Instruments, 64-0715) in standard growth media (DMEM-HG (Invitrogen, 11960), sodium pyruvate (Invitrogen, 11360), GlutaMAX (Invitrogen, 35050) and 10% heat inactivated fetal bovine serum (Invitrogen, 11082)). To stain the samples for microtubules, cells were fixed in with a mixture of 0.5% glutaraldeyde, 0.37% formaldehyde, and 0.3% Triton X-100 in Cytosketetal Buffer (CB, 10 mM MOPS, 138 mM KCl, 2 mM $MgCl_2$, 2 mM EGTA, 0.01% $NaN_3$, and 160 mM Sucrose, pH 6.1). After fixation, the cells were washed in CB, quenched with 100 nm glycine, washed in CB, and blicked in antibody dilution buffer (AbDil, 150 mM NaCl, 20 nM Tris, 0.1% Triton X-100, 0.1% $NaN_3$, and 2% bovine serum albumin, pH 7.4). The primary monoclonal antibody (Invitrogen, 32-2500) was incubated with the cells diluted to 2 µg/mL in AbDil for one hour at room temperature. Following primary antibody incubation, the cells were washed in the phosphor-buffered saline before incubating the cells with the secondary, Alexa Fluor 488 labeled antibody (Invitrogen, A-11001) at 1:200 dilution in AbDil for 1 hour.

Samples for dual-color experiments were initially stained with Mitotracker Red (Invitrogen, M-7512) as per the manufacturer's instruction prior to fixation. After mitochondrial labeling, the procedure outline above was used to stain the microtubules. All samples were mounted in fluoromount G (Electron Microscopy Solutionis, 17984-25) to a standard 25 mm×75 mm glass slide (SPI supplieds, #01251-AB) and sealed with nail polish.

a) Subdiffractive Beads

Yellow-green or red fluorescent beads (Invitrogen, F8803, 110 nm diameter; Invitrogen F8801, 100 nm diameter) were used for all point spread function (PSF) measurements. Beads were diluted from the stock concentration of 1:1300 (1:200 in distilled water and 1:13 in ethanol) and spread over cleaned glass coverslips. After air-drying for 5 minutes to evaporate the ethanol, coverslips were washed twice in distilled water to remove unattached beads. After air-drying again, the beads were mounted in fluoromount or silicone oil onto glass slides, and sealed with nail polish.

b) Zebrafish Samples

Tg(XIEef1a1:dclk2-GFP)$^{io0008}$ embryos carrying the zebrafish dclk2-GFP transgene were used in thick MSIM experiments shown in FIGS. 16A and 16B. To construct, this line, plasmids containing the transgene were injected into one-cell zebrafish embryos along with Tol2 mRNA. Fluorescent embryos were raised to adulthood and crossed to select for germline transmission by screening the offspring for GFP expression.

Tg(XIEdf1a1:dclk2-GFP)$^{io0008}$ embryos were collected by natural spawning and maintained at 28 degrees Centigrade. Prior to imaging by the multi-focal SIM system 200, embryos at 24 hpf were anesthetized in Tricaine (Sigma, E105210 at a final concentration of 600 µM in embryo media (60 mg Instant ocean sea salt (Petsmart) per liter $ddH_2O$). Anesthetized embryos were mounted on round coverslips, immobilized in 1% low-melt agarose (Cambrex, 50080), placed in a round coverslip holder (ASI, I-3033-25D), covered with embryo media, and imaged at room temperature.

Data Processing

Following acquisition of raw images using the illumination and microscope system described above, each set of collected raw images of the samples were processed into a super-resolution image using the processing system 225 having software written in the Python programming language. The processing steps employed by the processing system 225 were: (i) Automatic lattice detection to precisely determine the respective locations of the illumination spots;

(ii) Digital pinhole masking around each detected illumination spot to reject out-of-focus light, and optical flat-fielding using calibration data; (iii) Local contraction (e.g., scaling), and re-sampling the area around each illumination spot to improve the resolution by $\sqrt{2}$; (iv) Summing the processed raw images to produce a super-resolution composite image; and (v) Using conventional deconvolution techniques to recover the full 2× resolution enhancement. These process steps are discussed in greater detail above with respect to the focusing, scaling, and summing operation 210 executed by the processing system 225 of the multi-focal SIM system 200.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A microscopy system comprising:
    a light source for transmitting a single light beam;
    a beam splitter for splitting the single light beam into a plurality of light beams forming a plurality of multi-focal patterns, wherein each of the multi-focal patterns defines a plurality of focal points;
    a scanner for scanning the plurality of light beams that forms each of the multi-focal patterns onto a sample such that the sample generates a plurality of multi-focal fluorescent emissions in each of the multi-focal patterns that defines a plurality of fluorescence focal points;
    a detector for collecting the plurality of multi-focal fluorescent emissions that results from each of the multi-focal patterns; and
    a processing system for processing the plurality of multi-focal fluorescent emissions that results from each of the multi-focal patterns collected from the detector comprising:
        a processor in operative communication with a database for storing the plurality of collected multi-focal fluorescent emissions resulting from the multi-focal patterns, wherein the processor removes out-of-focus fluorescent emissions for each of the plurality of fluorescent emission to leave only in-focus fluorescent emissions resulting from each of the plurality of multi-focal patterns, wherein the processor then scales the in-focus fluorescence emissions resulting from each of the plurality of multi-focal patterns in a local contraction operation to produce scaled, in-focus fluorescent emissions; wherein the processor sums each scaled, in-focus fluorescence emissions to produce a composite image.

2. The microscopy system of claim 1, further comprising the processor executing a deconvolution operation for processing the plurality of multi-focal patterns with the scaled, in-focus fluorescent emissions.

3. The microscopy system of claim 2, wherein the deconvolution operation performs a de-blurring operation to the composite image.

4. The microscopy system of claim 1, wherein the beam splitter comprises a digital micromirror device or a swept-field confocal unit, or a spinning-disk, or a Nipkow confocal scan head.

5. The microscopy system of claim 1, wherein the processing system executes an automatic lattice detection of each of the plurality of multi-focal patterns to determine the position of one or more illumination spots.

6. The microscopy system of claim 5, wherein the automatic lattice detection determines a plurality of vectors to locate the position of each of the one or more illumination spots.

7. The microscopy system of claim 6, wherein the plurality of vectors comprises lattice vectors, shift vectors, and/or offset vectors.

8. The microscopy system of claim 7, wherein two of the lattice vectors specify a two-dimensional displacement between any two neighboring illumination spots.

9. The microscopy system of claim 8, wherein the two of the lattice vectors specify a two-dimensional displacement between any two neighboring illumination sports such that any lattice point displaced by any of the lattice vectors will fall on another lattice point.

10. The microscopy system of claim 5, wherein the automatic lattice detection determines a plurality of vectors to specify the location of all focal points for each multi-focal fluorescent emission.

11. The microscopy system of claim 10, wherein the automatic lattice detection determines five vectors to specify the location of all the focal points for each multi-focal fluorescent emission.

12. The microscopy system of claim 1, wherein the processor scales the in-focus fluorescence emissions resulting from each of the plurality of multi-focal patterns in a local contraction operation in which each of the plurality of fluorescent focal points resulting from each of the multi-focal patterns maintains the same distance from another plurality of fluorescent focal points resulting from the multi-focal pattern as the plurality of fluorescent focal points contract.

13. The microscopy system of claim 5, wherein the one or more illumination spots comprise one or more focal points.

14. A microscopy system comprising:
    a light source for transmitting a single light beam;
    a beam splitter for splitting the single light beam into a plurality of light beams forming a plurality of multi-focal patterns, wherein each of the multi-focal patterns defines a plurality of focal points;
    a scanner for scanning the plurality of light beams that forms each of the multi-focal patterns onto a sample such that the sample generates a plurality of multi-focal fluorescent emissions in each of the multi-focal patterns that defines a plurality of fluorescence focal points;
    a detector for collecting the plurality of multi-focal fluorescent emissions that results from each of the multi-focal patterns; and
    a processing system for processing the plurality of multi-focal fluorescent emissions that results from each of the multi-focal patterns collected from the detector comprising:
        a processor in operative communication with a database for storing the plurality of collected multi-focal fluorescent emissions resulting from the multi-focal patterns, wherein the processor removes out-of-focus fluorescent emissions for each of the plurality of fluorescent emission to leave only in-focus fluorescent emissions resulting from each of the plurality of multi-focal patterns.

15. The microscopy system of claim 14, further comprising the processor executing a deconvolution operation for processing the plurality of multi-focal patterns with the scaled, in-focus fluorescent emissions.

16. The microscopy system of claim 14, wherein the beam splitter comprises a digital micromirror device or a swept-field confocal unit, or a spinning-disk, or a Nipkow confocal scan head.

17. The microscopy system of claim 14, wherein the processing system executes an automatic lattice detection of each of the plurality of multi-focal patterns to determine the position of one or more illumination spots.

18. The microscopy system of claim 14, wherein the automatic lattice detection determines a plurality of vectors to locate the position of each of the one or more illumination spots.

19. The microscopy system of claim 18, wherein the plurality of vectors comprises lattice vectors, shift vectors, and/or offset vectors.

20. The microscopy system of claim 19, wherein two of the lattice vectors specify a two-dimensional displacement between any two neighboring illumination spots.

\* \* \* \* \*